United States Patent
List et al.

(10) Patent No.: US 12,319,685 B2
(45) Date of Patent: Jun. 3, 2025

(54) SMALL MOLECULE PYRIN-DOMAIN TARGETED NLRP3 INFLAMMASOME INHIBITORS

(71) Applicant: H. LEE MOFFITT CANCER CENTER AND RESEARCH INSTITUTE, INC., Tampa, FL (US)

(72) Inventors: Alan List, Tampa, FL (US); Haitao Ji, Tampa, FL (US)

(73) Assignee: H. LEE MOFFITT CANCER CENTER AND RESEARCH INSTITUTE, INC., Tampa, FL (US)

(*) Notice: Subject to any disclaimer, the term of this patent is extended or adjusted under 35 U.S.C. 154(b) by 1065 days.

(21) Appl. No.: 17/268,983

(22) PCT Filed: Aug. 15, 2019

(86) PCT No.: PCT/US2019/046637
§ 371 (c)(1),
(2) Date: Feb. 17, 2021

(87) PCT Pub. No.: WO2020/037116
PCT Pub. Date: Feb. 20, 2020

(65) Prior Publication Data
US 2022/0098188 A1 Mar. 31, 2022

Related U.S. Application Data

(60) Provisional application No. 62/719,199, filed on Aug. 17, 2018.

(51) Int. Cl.
| C07D 471/04 | (2006.01) |
| C07D 213/85 | (2006.01) |
| C07D 277/56 | (2006.01) |
| C07D 277/68 | (2006.01) |
| C07D 519/00 | (2006.01) |

(52) U.S. Cl.
CPC ......... *C07D 471/04* (2013.01); *C07D 213/85* (2013.01); *C07D 277/56* (2013.01); *C07D 277/68* (2013.01); *C07D 519/00* (2013.01)

(58) Field of Classification Search
CPC ... C07D 233/52; A61K 31/4166; A61P 31/04; A61P 31/10
See application file for complete search history.

(56) References Cited

U.S. PATENT DOCUMENTS

| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 5,167,649 A | 12/1992 | Zook |
| 6,960,648 B2 | 11/2005 | Bonny |
| 2002/0035243 A1 | 3/2002 | Imfeld et al. |
| 2002/0120100 A1 | 8/2002 | Bonny |
| 2003/0032594 A1 | 2/2003 | Bonny |
| 2016/0052876 A1 | 2/2016 | Abbate et al. |

OTHER PUBLICATIONS

Hamaguchi et al., "Synthesis of 1,3-Disubstituted-1,2,3,4-tetrahydro-beta-carboline Derivative, and Studies on Their Stereoisomers." Yakugakuu Zasshi, vol. 94(3), pp. 351-358 (Year: 1974).*
International Search Report and Written Opinion in PCT/US2019/046637. Mailed Oct. 24, 2019. 9 pages.
Pubchem CID 56946231, pp. 1-6, Apr. 23, 2012: p. 2, 2D structure.
Pubchem CID 5280953, pp. pp. 1-26, Mar. 25, 2005; entire document.
Tong, B. et al. Sinomenine induces the generation of intestinal Treg cells and attenuates arthritis via activation of aryl hydrocarbon receptor, Laboratory Investigation 96.
Huai, W. et al., Aryl hydrocarbon receptor negatively regulates NLRP3 inflammasome activity by inhibiting NLRP3 transcription, Nature Communications 5.
Abais, J.M., Xia, M., Zhang, Y., Boini, K.M., and Li, P.L. (2015). Redox regulation of NLRP3 inflammasomes: ROS as trigger or effector? Antioxid Redox Signal 22, 1111-1129.
Bae, J.Y., and Park, H.H. (2011a). Crystal structure of NALP3 protein pyrin domain (PYD) and its implications in inflammasome assembly. J Biol Chem 286, 39528-39536.
Bae, J.Y., and Park, H.H. (2011b). Crystallization and preliminary X-ray crystallographic studies of the PYD domain of human NALP3. Acta crystallographica Section F, Structural biology and crystallization communications 67, 1421-1424.
Baroja-Mazo, A., Martín-Sánchez, F., Gomez, A.I., Martínez, C.M., Amores-Iniesta, J., Compan, V., Barberà-Cremades, M., Yagüe, J., Ruiz-Ortiz, E., Antón, J., et al. (2014). The NLRP3 inflammasome is released as a particulate danger signal that amplifies the inflammatory response. Nat Immunol 15, 738-748.
Basiorka, A.A., McGraw, K.L., Eksioglu, E.A., Chen, X., Johnson, J., Zhang, L., Zhang, Q., Irvine, B.A., Cluzeau, T., Sallman, D.A., et al. (2016). The NLRP3 inflammasome functions as a driver of the myelodysplastic syndrome phenotype. Blood 128, 2960-2975.
Bedoya, F., Sandler, L.L., and Harton, J.A. (2007). Pyrin-only protein 2 modulates NF-κB and disrupts ASC:CLR interactions. J Immunol 178, 3837-3845.
Bejar, R., Stevenson, K., Abdel-Wahab, O., Galili, N., Nilsson, B., Garcia-Manero, G., Kantarjian, H., Raza, A., Levine, R.L., Neuberg, D., et al. (2011). Clinical effect of point mutations in myelodysplastic syndromes. The New England journal of medicine 364, 2496-2506.
Bergsbaken, T., Fink, S.L., and Cookson, B.T. (2009). Pyroptosis: host cell death and inflammation. Nat Rev Microbiol 7, 99-109.

(Continued)

*Primary Examiner* — Barbara P Badio
(74) *Attorney, Agent, or Firm* — Meunier Carlin & Curfman LLC

(57) ABSTRACT

Disclosed herein are small molecule pyrin-domain targeted NLRP3 inflammasome inhibitors.

13 Claims, No Drawings

(56) References Cited

OTHER PUBLICATIONS

Bird, G.H., Bernal, F., Pitter, K., and Walensky, L.D. (2008). Synthesis and biophysical characterization of stabilized alpha-helices of BCL-2 domains. Methods in enzymology 446, 369-386.
Boldin, M.P., Taganov, K.D., Rao, D.S., Yang, L., Zhao, J.L., Kalwani, M., Garcia-Flores, Y., Luong, M., Devrekanli, A., Xu, J., et al. (2011). miR-146a is a significant brake on autoimmunity, myeloproliferation, and cancer in mice. J Exp Med 208, 1189-1201.
Braun, T., Carvalho, G., Coquelle, A., Vozenin, M.-C., Lepelley, P., Hirsch, F., Kiladjian, J.-J., Ribrag, V., Fenaux, P., and Kroemer, G. (2006). NF-κB constitutes a potential therapeutic target in high-risk myelodysplastic syndrome. Blood 107, 1156-1165.
Broz, P., and Dixit, V.M. (2016). Inflammasomes: mechanism of assembly, regulation and signalling. Nat Rev Immunol 16, 407-420.
Cai, X., Chen, J., Xu, H., Liu, S., Jiang, Q.-X., Halfmann, R., and Chen, Z.J. (2014). Prion-like polymerization underlies signal transduction in antiviral immune defense and inflammasome activation. Cell 156, 1207-1222.
Chen, X., Eksioglu, E.A., Zhou, J., Zhang, L., Djeu, J., Fortenbery, N., Epling-Burnette, P., Van Bijnen, S., Dolstra, H., Cannon, J., et al. (2013). Induction of myelodysplasia by myeloid-derived suppressor cells. J Clin Invest 123, 4595-4611.
Chen, Z., Martin, M., Li, Z., and Shyy, J.Y.-J. (2014). Endothelial dysfunction: the role of sterol regulatory element-binding protein-induced NOD-like receptor family pyrin domain-containing protein 3 inflammasome in atherosclerosis. Curr Opin Lipidol 25, 339-349.
Choi, J.Y., Kim, C.M., Seo, E.K., Bhat, E.A., Jang, T.-h., Lee, J.H., and Park, H.H. (2015). Crystal structure of human POP1 and its distinct structural feature for PYD domain. Biochem Biophys Res Commun 460, 957-963.
Chu, Q., Moellering, R.E., Hilinski, G.J., Kim, Y.-W., Grossmann, T.N., Yeh, J.T.-H., and Verdine, G.L. (2015). Towards understanding cell penetration by stapled peptides. MedChemComm 6, 111-119.
Coll, R.C., Robertson, A., Butler, R., Cooper, M., and O'Neill, L.A. (2011). The cytokine release inhibitory drug CRID3 targets ASC oligomerisation in the NLRP3 and AIM2 inflammasomes. PLoS One 6, e29539.
Coll, R.C., Robertson, A.A.B., Chae, J.J., Higgins, S.C., Muñoz-Planillo, R., Inserra, M.C., Vetter, I., Dungan, L.S., Monks, B.G., Stutz, A., et al. (2015). A small-molecule inhibitor of the NLRP3 inflammasome for the treatment of inflammatory diseases. Nat Med 21, 248-255.
Daniels, M.J.D., Rivers-Auty, J., Schilling, T., Spencer, N.G., Watremez, W., Fasolino, V., Booth, S.J., White, C.S., Baldwin, A.G., Freeman, S., et al. (2016). Fenamate NSAIDs inhibit the NLRP3 inflammasome and protect against Alzheimer's disease in rodent models. Nature communications 7, 12504.
De Alba, E. (2009). Structure and interdomain dynamics of apoptosis-associated speck-like protein containing a CARD (ASC). J Biol Chem 284, 32932-32941.
De Almeida, L., Khare, S., Misharin, A.V., Patel, R., Ratsimandresy, R.A., Wallin, M.C., Perlman, H., Greaves, D.R., Hoffman, H.M., Dorfleutner, A., et al. (2015). The Pyrin domain-only protein POP1 inhibits inflammasome assembly and ameliorates inflammatory disease. Immunity 43, 264-276.
Dick, M.S., Sborgi, L., Rühl, S., Hiller, S., and Broz, P. (2016). ASC filament formation serves as a signal amplification mechanism for inflammasomes. Nature communications 7, 11929.
Dorfleutner, A., Bryan, N.B., Talbott, S.J., Funya, K.N., Rellick, S.L., Reed, J.C., Shi, X., Rojanasakul, Y., Flynn, D.C., and Stehlik, C. (2007a). Cellular pyrin domain-only protein 2 is a candidate regulator of inflammasome activation. Infect Immun 75, 1484-1492.
Dorfleutner, A., Talbott, S.J., Bryan, N.B., Funya, K.N., Rellick, S.L., Reed, J.C., Shi, X., Rojanasakul, Y., Flynn, D.C., and Stehlik, C. (2007b). A Shope Fibroma virus Pyrin-only protein modulates the host immune response. Virus Genes 35, 685-694.
Dougherty, D.A. (1996). Cation-π interactions in chemistry and biology: a new view of benzene, Phe, Tyr, and Trp. Science 271, 163-168.
Dougherty, D.A. (2013). The cation-π interaction. Accounts of chemical research 46, 885-893.
Doyle, S.L., Campbell, M., Ozaki, E., Salomon, R.G., Mori, A., Kenna, P.F., Farrar, G.J., Kiang, A.-S., Humphries, M.M., Lavelle, E.C., et al. (2012). NLRP3 has a protective role in age-related macular degeneration through the induction of IL-18 by drusen components. Nat Med 18, 791-798.
Ehrchen, J.M., Sunderkötter, C., Foell, D., Vogl, T., and Roth, J. (2009). The endogenous Toll-like receptor 4 agonist S100A8/S100A9 (calprotectin) as innate amplifier of infection, autoimmunity, and cancer. J Leukoc Biol 86, 557-566.
Epling-Burnette, P.K., McDaniel, J., Wei, S., and List, A.F. (2012). Emerging immunosuppressive drugs in myelodysplastic syndromes. Expert Opin Emerg Drugs 17, 519-541.
Fang, J., Barker, B., Bolanos, L., Liu, X., Jerez, A., Makishima, H., Christie, S., Chen, X., Rao, D.S., Grimes, H.L., et al. (2014). Myeloid malignancies with chromosome 5q deletions acquire a dependency on an intrachromosomal NF-κB gene network. Cell Rep 8, 1328-1338.
Fang, J., Rhyasen, G., Bolanos, L., Rasch, C., Varney, M., Wunderlich, M., Goyama, S., Jansen, G., Cloos, J., Rigolino, C., et al. (2012). Cytotoxic effects of bortezomib in myelodysplastic syndrome/acute myeloid leukemia depend on autophagy-mediated lysosomal degradation of TRAF6 and repression of PSMA1. Blood 120, 858-867.
Farquhar, M.J., and Bowen, D.T. (2003). Oxidative stress and the myelodysplastic syndromes. Int J Hematol 77, 342-350.
Fernandes-Alnemri, T., Wu, J., Yu, J.-W., Datta, P., Miller, B., Jankowski, W., Rosenberg, S., Zhang, J., and Alnemri, E.S. (2007). The pyroptosome: a supramolecular assembly of ASC dimers mediating inflammatory cell death via caspase-1 activation. Cell death and differentiation 14, 1590-1604.
Fowler, B.J., Gelfand, B.D., Kim, Y., Kerur, N., Tarallo, V., Hirano, Y., Amarnath, S., Fowler, D.H., Radwan, M., Young, M.T., et al. (2014). Nucleoside reverse transcriptase inhibitors possess intrinsic anti-inflammatory activity. Science 346, 1000-1003.
Franklin, B.S., Bossaller, L., De Nardo, D., Ratter, J.M., Stutz, A., Engels, G., Brenker, C., Nordhoff, M., Mirandola, S.R., Al-Amoudi, A., et al. (2014). The adaptor ASC has extracellular and 'prionoid' activities that propagate inflammation. Nat Immunol 15, 727-737.
Fulp, J., He, L., Toldo, S., Jiang, Y., Boice, A., Guo, C., Li, X., Rolfe, A., Sun, D., Abbate, A., et al. (2018). Structural Insights of Benzenesulfonamide Analogues as NLRP3 Inflammasome Inhibitors: Design, Synthesis, and Biological Characterization. Journal of medicinal chemistry 61, 5412-5423.
Gangat, N., Patnaik, M.M., and Tefferi, A. (2016). Myelodysplastic syndromes: contemporary review and how we treat. Am J Hematol 91, 76-89.
Greenberg P, Cox C, LeBeau MM, et al. International scoring system for evaluating prognosis in myelodysplastic syndromes. Blood 1997; 89:2079-2088.
Greenberg PL, Tuechler H, Schanz J, et al. Revised international prognostic scoring system for myelodysplastic syndromes. Blood 2012; 120:2454-2465.
Greenfield, N.J. (2006). Using circular dichroism spectra to estimate protein secondary structure. Nature protocols 1, 2876-2890.
Haferlach, T., Nagata, Y., Grossmann, V., Okuno, Y., Bacher, U., Nagae, G., Schnittger, S., Sanada, M., Kon, A., Alpermann, T., et al. (2014). Landscape of genetic lesions in 944 patients with myelodysplastic syndromes. Leukemia 28, 241-247.
Harijith, A., Ebenezer, D.L., and Natarajan, V. (2014). Reactive oxygen species at the crossroads of inflammasome and inflammation. Front Physiol 5, 352.
Hill, J.R., Coll, R.C., Sue, N., Reid, J.C., Dou, J., Holley, C.L., Pelingon, R., Dickinson, J.B., Biden, T.J., Schroder, K., et al. (2017). Sulfonylureas as Concomitant Insulin Secretagogues and NLRP3 Inflammasome Inhibitors. ChemMedChem 12, 1449-1457.
Hoss, F., Rodriguez-Alcazar, J.F., and Latz, E. (2017). Assembly and regulation of ASC specks. Cellular and molecular life sciences : CMLS 74, 1211-1229.
Jiang, H., He, H., Chen, Y., Huang, W., Cheng, J., Ye, J., Wang, A., Tao, J., Wang, C., Liu, Q., et al. (2017). Identification of a selective and direct NLRP3 inhibitor to treat inflammatory disorders. J Exp Med 214, 3219-3238.

(56) References Cited

OTHER PUBLICATIONS

Johnston, J.B., Barrett, J.W., Nazarian, S.H., Goodwin, M., Ricciuto, D., Wang, G., and McFadden, G. (2005). A poxvirus-encoded pyrin domain protein interacts with ASC-1 to inhibit host inflammatory and apoptotic responses to infection. Immunity 23, 587-598.
Kajla, S., Mondol, A.S., Nagasawa, A., Zhang, Y., Kato, M., Matsuno, K., Yabe-Nishimura, C., and Kamata, T. (2012). A crucial role for Nox 1 in redox-dependent regulation of Wnt-β-catenin signaling. FASEB J 26, 2049-2059.
Khare, S., Ratsimandresy, R.A., de Almeida, L., Cuda, C.M., Rellick, S.L., Misharin, A.V., Wallin, M.C., Gangopadhyay, A., Forte, E., Gottwein, E., et al. (2014). The Pyrin domain-only protein POP3 inhibits ALR inflammasomes and regulates responses to infection with DNA viruses. Nat Immunol 15, 343-353.
Klepin, H.D., Rao, A.V., and Pardee, T.S. (2014). Acute myeloid leukemia and myelodysplastic syndromes in older adults. Journal of clinical oncology : official journal of the American Society of Clinical Oncology 32, 2541-2552.
Koike, M., Ishiyama, T., Tomoyasu, S., and Tsuruoka, N. (1995). Spontaneous cytokine overproduction by peripheral blood mononuclear cells from patients with myelodysplastic syndromes and aplastic anemia. Leuk Res 19, 639-644.
Laliberte, R.E., Perregaux, D.G., Hoth, L.R., Rosner, P.J., Jordan, C.K., Peese, K.M., Eggler, J.F., Dombroski, M.A., Geoghegan, K.F., and Gabel, C.A. (2003). Glutathione s-transferase omega 1-1 is a target of cytokine release inhibitory drugs and may be responsible for their effect on interleukin-1β posttranslational processing. J Biol Chem 278, 16567-16578.
Lamkanfi, M., and Dixit, V.M. (2012). Inflammasomes and their roles in health and disease. Annu Rev Cell Dev Biol 28, 137-161.
Lamkanfi, M., and Dixit, V.M. (2014). Mechanisms and functions of inflammasomes. Cell 157, 1013-1022.
Lamkanfi, M., Mueller, J.L., Vitari, A.C., Misaghi, S., Fedorova, A., Deshayes, K., Lee, W.P., Hoffman, H.M., and Dixit, V.M. (2009). Glyburide inhibits the Cryopyrin/Nalp3 inflammasome. J Cell Biol 187, 61-70.
Latz, E., Xiao, T.S., and Stutz, A. (2013). Activation and regulation of the inflammasomes. Nat Rev Immunol 13, 397-411.
Liepinsh, E., Barbals, R., Dahl, E., Sharipo, A., Staub, E., and Otting, G. (2003). The death-domain fold of the ASC Pyrin domain, presenting a basis for Pyrin/Pyrin recognition. J Mol Biol 332, 1155-1163.
Lindsley, R.C., Saber, W., Mar, B.G., Redd, R., Wang, T., Haagenson, M.D., Grauman, P.V., Hu, Z.-H., Spellman, S.R., Lee, S.J., et al. (2017). Prognostic mutations in myelodysplastic syndrome after stem-cell transplantation. The New England journal of medicine 376, 536-547.
Lönn, P., and Dowdy, S.F. (2015). Cationic PTD/CPP-mediated macromolecular delivery: charging into the cell. Expert opinion on drug delivery 12, 1627-1636.
Lu, A., Magupalli, V.G., Ruan, J., Yin, Q., Atianand, M.K., Vos, M.R., Schröder, G.F., Fitzgerald, K.A., Wu, H., and Egelman, E.H. (2014). Unified polymerization mechanism for the assembly of ASC-dependent inflammasomes. Cell 156, 1193-1206.
Man, S.M., and Kanneganti, T.-D. (2016). Converging roles of caspases in inflammasome activation, cell death and innate immunity. Nat Rev Immunol 16, 7-21.
Maratheftis, C.I., Andreakos, E., Moutsopoulos, H.M., and Voulgarelis, M. (2007). Toll-like receptor-4 is up-regulated in hematopoietic progenitor cells and contributes to increased apoptosis in myelodysplastic syndromes. Clin Cancer Res 13, 1154-1160.
Marchetti, C., Chojnacki, J., Toldo, S., Mezzaroma, E., Tranchida, N., Rose, S.W., Federici, M., Van Tassell, B.W., Zhang, S., and Abbate, A. (2014). A novel pharmacologic inhibitor of the NLRP3 inflammasome limits myocardial injury after ischemia-reperfusion in the mouse. J Cardiovasc Pharmacol 63, 316-322.
Masters, S.L., Dunne, A., Subramanian, S.L., Hull, R.L., Tannahill, G.M., Sharp, F.A., Becker, C., Franchi, L., Yoshihara, E., Chen, Z., et al. (2010). Activation of the NLRP3 inflammasome by islet amyloid polypeptide provides a mechanism for enhanced IL-1β in type 2 diabetes. Nat Immunol 11, 897-904.
Mundle, S.D., Venugopal, P., Cartlidge, J.D., Pandav, D.V., Broady-Robinson, L., Gezer, S., Robin, E.L., Rifkin, S.R., Klein, M., Alston, D.E., et al. (1996). Indication of an involvement of interleukin-1β converting enzyme-like protease in intramedullary apoptotic cell death in the bone marrow of patients with myelodysplastic syndromes. Blood 88, 2640-2647.
Muñoz-Planillo, R., Kuffa, P., Martínez-Colón, G., Smith, B.L., Rajendiran, T.M., and Núñez, G. (2013). K+ efflux is the common trigger of NLRP3 inflammasome activation by bacterial toxins and particulate matter. Immunity 38, 1142-1153.
Natarajan, A., Ghose, R., and Hill, J.M. (2006). Structure and dynamics of ASC2, a pyrin domain-only protein that regulates inflammatory signaling. J Biol Chem 281, 31863-31875.
Nikolovska-Coleska, Z., Wang, R., Fang, X., Pan, H., Tomita, Y., Li, P., Roller, P.P., Krajewski, K., Saito, N.G., Stuckey, J.A., et al. (2004). Development and optimization of a binding assay for the XIAP BIR3 domain using fluorescence polarization. Analytical biochemistry 332, 261-273.
O'Brien, M., Moehring, D., Muñoz-Planillo, R., Núñez, G., Callaway, J., Ting, J., Scurria, M., Ugo, T., Bernad, L., Cali, J., et al. (2017). A bioluminescent caspase-1 activity assay rapidly monitors inflammasome activation in cells. Journal of immunological methods 447, 1-13.
Oroz, J., Barrera-Vilarmau, S., Alfonso, C., Rivas, G., and de Alba, E. (2016). ASC pyrin domain self-associates and binds NLRP3 protein using equivalent binding interfaces. J Biol Chem 291, 19487-19501.
Ortmann, C.A., Kent, D.G., Nangalia, J., Silber, Y., Wedge, D.C., Grinfeld, J., Baxter, E.J., Massie, C.E., Papaemmanuil, E., Menon, S., et al. (2015). Effect of mutation order on myeloproliferative neoplasms. The New England journal of medicine 372, 601-612.
Papaemmanuil, E., Gerstung, M., Malcovati, L., Tauro, S., Gundem, G., Van Loo, P., Yoon, C.J., Ellis, P., Wedge, D.C., Pellagatti, A., et al. (2013). Clinical and biological implications of driver mutations in myelodysplastic syndromes. Blood 122, 3616-3627; quiz 3699.
Perregaux, D.G., McNiff, P., Laliberte, R., Hawryluk, N., Peurano, H., Stam, E., Eggler, J., Griffiths, R., Dombroski, M.A., and Gabel, C.A. (2001). Identification and characterization of a novel class of interleukin-1 post-translational processing inhibitors. J Pharmacol Exp Ther 299, 187-197.
Porter, K.A., Duffy, E.B., Nyland, P., Atianand, M.K., Sharifi, H., and Harton, J.A. (2014). The CLRX.1/NOD24 (NLRP2P) pseudogene codes a functional negative regulator of NF-kappaB, pyrin-only protein 4. Genes and immunity 15, 392-403.
Pyatt, D.W., Stillman, W.S., Yang, Y., Gross, S., Zheng, J.H., and Irons, R.D. (1999). An essential role for NF-κB in human CD34+ bone marrow cell survival. Blood 93, 3302-3308.
Rassool, F.V., Gaymes, T.J., Omidvar, N., Brady, N., Beurlet, S., Pla, M., Reboul, M., Lea, N., Chomienne, C., Thomas, N.S.B., et al. (2007). Reactive oxygen species, DNA damage, and error-prone repair: a model for genomic instability with progression in myeloid leukemia? Cancer Res 67, 8762-8771.
Rathinam, V.A., and Fitzgerald, K.A. (2016). Inflammasome complexes: emerging mechanisms and effector functions. Cell 165, 792-800.
Rathinam, V.A., Vanaja, S.K., and Fitzgerald, K.A. (2012). Regulation of inflammasome signaling. Nat Immunol 13, 333-342.
Reboldi, A., Dang, E.V., McDonald, J.G., Liang, G., Russell, D.W., and Cyster, J.G. (2014). Inflammation. 25-Hydroxycholesterol suppresses interleukin-1-driven inflammation downstream of type I interferon. Science 345, 679-684.
Rharass, T., Lemcke, H., Lantow, M., Kuznetsov, S.A., Weiss, D.G., and Panakova, D. (2014). Ca2+-mediated mitochondrial reactive oxygen species metabolism augments Wnt/β-catenin pathway activation to facilitate cell differentiation. J Biol Chem 289, 27937-27951.
Rhyasen, G.W., Bolanos, L., Fang, J., Jerez, A., Wunderlich, M., Rigolino, C., Mathews, L., Ferrer, M., Southall, N., Guha, R., et al. (2013). Targeting IRAK1 as a therapeutic approach for myelodysplastic syndrome. Cancer Cell 24, 90-104.

(56) References Cited

OTHER PUBLICATIONS

Sallmyr, A., Fan, J., and Rassool, F.V. (2008). Genomic instability in myeloid malignancies: increased reactive oxygen species (ROS), DNA double strand breaks (DSBs) and error-prone repair. Cancer Lett 270, 1-9.

Sawanobori, M., Yamaguchi, S., Hasegawa, M., Inoue, M., Suzuki, K., Kamiyama, R., Hirokawa, K., and Kitagawa, M. (2003). Expression of TNF receptors and related signaling molecules in the bone marrow from patients with myelodysplastic syndromes. Leuk Res 27, 583-591.

Sborgi, L., Ravotti, F., Dandey, V.P., Dick, M.S., Mazur, A., Reckel, S., Chami, M., Scherer, S., Huber, M., Böckmann, A., et al. (2015). Structure and assembly of the mouse ASC inflammasome by combined NMR spectroscopy and cryo-electron microscopy. Proc Natl Acad Sci U S A 112, 13237-13242.

Schneider, R.K., Schenone, M., Ferreira, M.V., Kramann, R., Joyce, C.E., Hartigan, C., Beier, F., Brummendorf, T.H., Germing, U., Platzbecker, U., et al. (2016). Rps14 haploinsufficiency causes a block in erythroid differentiation mediated by S100A8 and S100A9. Nat Med 22, 288-297.

Schroder, K., and Tschopp, J. (2010). The inflammasomes. Cell 140, 821-832.

Sharma, D., and Kanneganti, T.-D. (2016). The cell biology of inflammasomes: mechanisms of inflammasome activation and regulation. J Cell Biol 213, 617-629.

Shetty, V., Mundle, S., Alvi, S., Showel, M., Broady-Robinson, L., Dar, S., Borok, R., Showel, J., Gregory, S., Rifkin, S., et al. (1996). Measurement of apoptosis, proliferation and three cytokines in 46 patients with myelodysplastic syndromes. Leuk Res 20, 891-900.

Simard, J.-C., Cesaro, A., Chapeton-Montes, J., Tardif, M., Antoine, F., Girard, D., and Tessier, P.A. (2013). S100A8 and S100A9 induce cytokine expression and regulate the NLRP3 inflammasome via ROS-dependent activation of NF-κB1. PLoS One 8, e72138.

Starczynowski, D.T., Kuchenbauer, F., Argiropoulos, B., Sung, S., Morin, R., Muranyi, A., Hirst, M., Hogge, D., Marra, M., Wells, R.A., et al. (2010). Identification of miR-145 and miR-146a as mediators of the 5q-syndrome phenotype. Nat Med 16, 49-58.

Stehlik, C., Krajewska, M., Welsh, K., Krajewski, S., Godzik, A., and Reed, J.C. (2003). The PAAD/Pyrin-only protein POP1/ASC2 is a modulator of ASC-mediated nuclear-factor-κB and pro-caspase-1 regulation. Biochem J 373, 101-113.

Stutz, A., Horvath, G.L., Monks, B.G., and Latz, E. (2013). ASC speck formation as a readout for inflammasome activation. Methods in molecular biology (Clifton, NJ) 1040, 91-101.

Tang, T., Lang, X., Xu, C., Wang, X., Gong, T., Yang, Y., Cui, J., Bai, L., Wang, J., Jiang, W., et al. (2017). CLICs-dependent chloride efflux is an essential and proximal upstream event for NLRP3 inflammasome activation. Nature communications 8, 202.

Tefferi, A., and Vardiman, J.W. (2009). Myelodysplastic syndromes. The New England journal of medicine 361, 1872-1885.

Vajjhala, P.R., Mirams, R.E., and Hill, J.M. (2012). Multiple binding sites on the pyrin domain of ASC protein allow self-association and interaction with NLRP3 protein. J Biol Chem 287, 41732-41743.

Vanaja, S.K., Rathinam, V.A.K., and Fitzgerald, K.A. (2015). Mechanisms of inflammasome activation: recent advances and novel insights. Trends Cell Biol 25, 308-315.

Velegraki, M., Papakonstanti, E., Mavroudi, I., Psyllaki, M., Tsatsanis, C., Oulas, A., Iliopoulos, I., Katonis, P., and Papadaki, H.A. (2013). Impaired clearance of apoptotic cells leads to HMGB1 release in the bone marrow of patients with myelodysplastic syndromes and induces TLR4-mediated cytokine production. Haematologica 98, 1206-1215.

Vogl, T., Tenbrock, K., Ludwig, S., Leukert, N., Ehrhardt, C., van Zoelen, M.A.D., Nacken, W., Foell, D., van der Poll, T., Sorg, C., et al. (2007). Mrp8 and Mrp14 are endogenous activators of Toll-like receptor 4, promoting lethal, endotoxin-induced shock. Nat Med 13, 1042-1049.

Wei, Y., Chen, R., Dimicoli, S., Bueso-Ramos, C., Neuberg, D., Pierce, S., Wang, H., Yang, H., Jia, Y., Zheng, H., et al. (2013a). Global H3K4me3 genome mapping reveals alterations of innate immunity signaling and overexpression of JMJD3 in human myelodysplastic syndrome CD34+ cells. Leukemia 27, 2177-2186.

Wei, Y., Dimicoli, S., Bueso-Ramos, C., Chen, R., Yang, H., Neuberg, D., Pierce, S., Jia, Y., Zheng, H., Wang, H., et al. (2013b). Toll-like receptor alterations in myelodysplastic syndrome. Leukemia 27, 1832-1840.

Welch, J.S., Petti, A.A., Miller, C.A., Fronick, C.C., O'Laughlin, M., Fulton, R.S., Wilson, R.K., Baty, J.D., Duncavage, E.J., Tandon, B., et al. (2016). TP53 and decitabine in acute myeloid leukemia and myelodysplastic syndromes. The New England journal of medicine 375, 2023-2036.

Wetzler, M., Kurzrock, R., Estrov, Z., Estey, E., and Talpaz, M. (1995). Cytokine expression in adherent layers from patients with myelodysplastic syndrome and acute myelogenous leukemia. Leuk Res 19, 23-34.

Yoshida, K., Sanada, M., Shiraishi, Y., Nowak, D., Nagata, Y., Yamamoto, R., Sato, Y., Sato-Otsubo, A., Kon, A., Nagasaki, M., et al. (2011). Frequent pathway mutations of splicing machinery in myelodysplasia. Nature 478, 64-69.

Yoshizato, T., Dumitriu, B., Hosokawa, K., Makishima, H., Yoshida, K., Townsley, D., Sato-Otsubo, A., Sato, Y., Liu, D., Suzuki, H., et al. (2015). Somatic mutations and clonal hematopoiesis in aplastic anemia. The New England journal of medicine 373, 35-47.

Youm, Y.-H., Nguyen, K.Y., Grant, R.W., Goldberg, E.L., Bodogai, M., Kim, D., D'Agostino, D., Planavsky, N., Lupfer, C., Kanneganti, T.D., et al. (2015). The ketone metabolite β-hydroxybutyrate blocks NLRP3 inflammasome-mediated inflammatory disease. Nat Med 21, 263-269.

Zhang, Y., Teuscher, K.B., and Ji, H. (2016). Direct alpha-heteroarylation of amides (alpha to nitrogen) and ethers through a benzaldehyde-mediated photoredox reaction. Chemical science 7, 2111-2118.

Zhao, J.L., Rao, D.S., Boldin, M.P., Taganov, K.D., O'Connell, R.M., and Baltimore, D. (2011). NF-κB dysregulation in microRNA-146a-deficient mice drives the development of myeloid malignancies. Proc Natl Acad Sci U S A 108, 9184-9189.

Zhao, J.L., Rao, D.S., O'Connell, R.M., Garcia-Flores, Y., and Baltimore, D. (2013). MicroRNA-146a acts as a guardian of the quality and longevity of hematopoietic stem cells in mice. Elife 2, e00537.

Zhou, R., Tardivel, A., Thorens, B., Choi, I., and Tschopp, J. (2010). Thioredoxin-interacting protein links oxidative stress to inflammasome activation. Nat Immunol 11, 136-140.

International Preliminary Report on Patentability issued for Application No. PCT/US2019/046637, dated Mar. 4, 2021.

\* cited by examiner

SMALL MOLECULE PYRIN-DOMAIN TARGETED NLRP3 INFLAMMASOME INHIBITORS

CROSS REFERENCE TO RELATED APPLICATIONS

This application is a United States National Phase Patent Application of International Patent Application Number PCT/US2019/046637, filed on Aug. 15, 2019, which claims the benefit of priority to U.S. Provisional Application No. 62/719,199, filed Aug. 17, 2018, which are incorporated by reference herein in their entirety.

FIELD

The disclosure generally relates to inflammatory diseases and small molecules used to treat inflammatory diseases.

BACKGROUND

Myelodysplastic syndrome (MDS) is a heterogeneous group of clonal hematopoietic stem cell disorders characterized by bone marrow cytological dysplasia, ineffective hematopoiesis, and a propensity to progress to acute myeloid leukemia (AML). Despite their shared clinical phenotypes, MDSs harbor a diverse array of clonal chromosome abnormalities and somatic gene mutations. Due to the high genetic heterogeneity of the disease and the limited understanding of the molecular abnormalities that contribute to the disease, none of the currently available treatments are curative for MDS.

The inflammation and innate immune system play an important role in the pathogenesis of MDS. Inflammatory cytokines such as interleukin-1β (IL-1β) and their receptors are significantly up-regulated in MDS. The interaction of the danger-associated molecular pattern (DAMP) heterodimer S100A8/9 with Toll-like receptor 4 (TLR4) and CD33 drives expansion of myeloid-derived suppressor cells (MDSCs) in bone marrow of MDS patients to produce hematopoietic suppressive cytokines. MDS hematopoietic stem and progenitor cells (HSPCs) overexpress key signal molecules of the TLR pathway and activate NF-κB, leading to peripheral blood cytopenias.

The activation of TLRs by DAMPs can trigger pyroptosis, a caspase-1-dependent lytic cell death. Pyroptosis is executed through the formation of inflammasome, a cytosolic, multiprotein complex that is composed of the sensor molecule, such as nucleotide-binding domain (NOD)-like receptor protein 3 (NLRP3), the adaptor protein ASC (apoptosis-associated speck-like protein with a CARD), and the effector protein pro-caspase 1. An inflammasome can activate inflammatory responses and promote maturation and secretion of pro-inflammatory cytokines such as interleukin 1β (IL-1β) and interleukin 18 (IL-18). Inflaminasome dysregulation can cause numerous diseases such as autoimmune diseases and auto-inflammatory diseases.

NLRP3 is composed of a central nucleotide-binding and oligomerization domain (NACHT), the N-terminal leucine-rich repeat (LRR), and the C-terminal pyrin domain (PYD). ASC consists of one CARD domain and one PYD domain. Pro-caspase 1 has the CARD and caspase 1 domains. When sensing the external stress signal, the auto-repressed NLRP3 opens up for oligomerization and forms a wheel-shaped signaling hub. The homotypic protein-protein interaction (PPI) between NLRP3 PYD domains (NLRP3$^{PYD}$) forms a disk at the center of this wheel-shaped hub. This NLRP3$^{PYD}$ disk then recruits ASC through the NLRP3$^{PYD}$/ASC$^{PYD}$ PPI. ASC CARD domain recruits the CARD domain of pro-caspase 1, allowing caspase 1 dimerization to form the active caspase 1. Caspase 1 catalyzes the conversion of precursors of the inflammatory cytokines IL-1β and IL-18 to their active forms(Bergsbaken et al., 2009)[1]. Correspondingly, pore formation occurs within the plasma membrane, leading to influx of cations and water, cell swelling, and ultimately osmotic lysis. List and co-workers dissected the role of NLRP3 inflammasome in driving pyroptotic cell death in MDS HSPCs through a series of in vitro and in vivo experiments.

The selective disruption of the NLRP3 inflammasome can offer targeted therapies to eliminate the MDS-initiating clones. Diarylsulfonylureas are known to inhibit caspase 1-dependent IL-1β processing (Perregaux et al., 2001). Among them, glyburide inhibits NLRP3 inflamasome activation (Lamkanfi et al., 2009; Marchetti et al., 2014; Masters et al., 2010). MCC950 (Coll et al., 2015) (also termed CRID3 and CP-456,773 (Coll et al., 2011)), another diarylsulfonylurea-containing compound, also inhibits both canonical and non-canonical activation of the NLRP3 inflammasome. Glutathione S-transferase omega 1-1 was identified as one target for its effects on IL-1β posttranslational processing (Laliberte et al., 2003). MCC950 inhibits NLRP3-induced ASC oligomerization and speck formation in mouse and human macrophages but did not prevent NLRP3 oligomerization or NLRP3/ASC interactions. Later, MCC950 was found to bind with the Walker B motif of the NACHT domain, block ATP hydrolysis, and maintain NLRP3 into the inactive conformation (Coll et al., 2019; Tapia-Abellan et al., 2019). MCC950 attenuated the severity of experimental autoimmune encephalitis, a mouse model of human multiple sclerosis and showed inhibitory effects in mouse models that mirror the human gain-of-function mutations in NLRP3 that lead to the auto-inflammatory Muckle-Wells syndrome (MWS). MCC950 also inhibited IL-1β production of peripheral blood mononuclear cells isolated from patients with MWS. Further structural modifications based on diarylsulfonylurea-containing inhibitors have been reported (Fulp et al., 2018; Hill et al., 2017).

β-Hydroxybutyrate (BHB), a ketone metabolite, inhibits NLRP3-induced ASC oligomerization and speck formation in human macrophages and exhibits in vivo activities using mouse models that have abnormal NLRP3 inflammasome function (Youm et al., 2015). BHB inhibits K$^+$ efflux (Munoz-Planillo et al., 2013), and its activity is independent of AMP-activated protein kinase, ROS, autophagy, or glycolytic inhibition. Nucleoside reverse transcriptase inhibitors such as zidovudine (AZT) blocks the activity of the ion channel P2X7 and inhibits P2X7-mediated NLRP3 inflammasome activation (Fowler et al., 2014).

25-Hydroxylcholesterol inhibits the function of transcription factor SREBP (sterol response element-binding protein) (Chen et al., 2014) and suppresses expression of the gene that encodes IL-1β (Reboldi et al., 2014).

The stimulation of NLRP3 induces oligomerization of NLRP3$^{PYD}$ (Lu et al., 2014; Sborgi et al., 2015). This oligomer recruits ASC through the NLRP3$^{PYD}$/ASC$^{PYD}$ PPI, resulting in prion nucleation. ASC prion then templates other ASC molecules to form a larger polymer through the ASC$^{PYD}$/ASC$^{PYD}$ PPI. This prion conversion is essential for NLRP3 inflammasome structure and its immune and inflammatory signaling (Cai et al., 2014). PYD only proteins (POPs), including POP1-POP4, are the endogenous negative regulators of the inflammasome (Dorfleutner et al., 2007a; Khare et al., 2014; Porter et al., 2014; Stehlik et al., 2003).

They bind with NLRP3 or ASC, inhibit PPIs within and between $NLRP3^{PYD}$ and $ASC^{PYD}$, preventing inflammasome assembly and signaling (Bedoya et al., 2007; de Almeida et al., 2015; Khare et al., 2014). Genetic loss of POPs increases IL-1β levels. Poxvirus that expressed a viral POP can block activation of inflammasomes and NF-κB, and suppress the host immune response (Dorfleutner et al., 2007b; Johnston et al., 2005).

The compositions and methods disclosed herein address these and other needs.

SUMMARY

Disclosed herein are small molecules which inhibit NLRP3 inflammasome assembly and thus can be used to treat diseases in which inflammasome formation is implicated such as inflammatory diseases. The small molecules can have a structure defined by Formula I or is a derivative thereof:

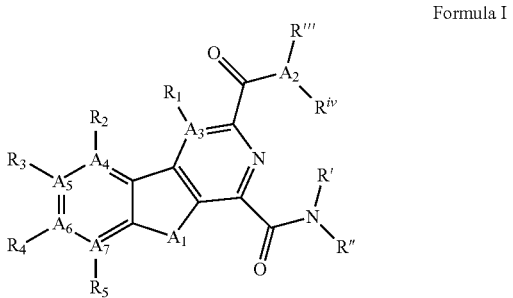

Formula I wherein $A_1$ is selected from O, $CH_2$, S, or NH;
$A_2$ is selected from O or N, wherein when $A_2$ is selected from O then $R^{iv}$ is absent;
$A_3$, $A_4$, $A_5$, $A_6$, or $A_7$ are independently selected from C, S, N;
R' and R" are independently selected from hydrogen; hydroxyl, substituted or unsubstituted $C_1$-$C_6$ alkyl, substituted or unsubstituted aminoalkyl, substituted or unsubstituted $C_1$-$C_6$ haloalkyl, substituted or unsubstituted cycloalkyl, substituted or unsubstituted cycloheteroalkyl, substituted or unsubstituted alkoxy, substituted or unsubstituted alkenyl, substituted or unsubstituted alkynyl, substituted or unsubstituted aryl, substituted or unsubstituted heteroaryl, or both R' and R" combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached;
R''' and $R^{iv}$ are independently selected from hydrogen; hydroxyl, substituted or unsubstituted $C_1$-$C_6$ alkyl, substituted or unsubstituted aminoalkyl, substituted or unsubstituted $C_1$-$C_6$ haloalkyl, substituted or unsubstituted cycloalkyl, substituted or unsubstituted cycloheteroalkyl, substituted or unsubstituted alkoxy, substituted or unsubstituted alkenyl, substituted or unsubstituted alkynyl, substituted or unsubstituted aryl, substituted or unsubstituted heteroaryl, or both R''' and $R^{iv}$ combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached;

$R_1$ is null or selected from hydrogen; hydroxyl, halide, substituted or unsubstituted nitrile, substituted or unsubstituted nitro, substituted or unsubstituted amine, substituted or unsubstituted alkyl halide, substituted or unsubstituted carboxyl, substituted or unsubstituted amide, substituted or unsubstituted ester, substituted or unsubstituted ether, substituted or unsubstituted ketone, substituted or unsubstituted $C_1$-$C_6$ alkyl, substituted or unsubstituted alkoxy, substituted or unsubstituted $C_2$-$C_6$ alkenyl, substituted or unsubstituted $C_2$-$C_6$ alkynyl, substituted or unsubstituted aryl, substituted or unsubstituted heteroaryl, substituted or unsubstituted silyl, substituted or unsubstituted sulfonyl, substituted or unsubstituted sulfone, substituted or unsubstituted sulfoxide, or substituted or unsubstituted thiol; and
$R_2$-$R_5$ are independently null or independently selected from hydrogen; hydroxyl, halide, substituted or unsubstituted nitrile, substituted or unsubstituted nitro, substituted or unsubstituted amine, substituted or unsubstituted alkyl halide, substituted or unsubstituted carboxyl, substituted or unsubstituted amide, substituted or unsubstituted ester, substituted or unsubstituted ether, substituted or unsubstituted ketone, substituted or unsubstituted $C_1$-$C_6$ alkyl, substituted or unsubstituted alkoxy, substituted or unsubstituted $C_2$-$C_6$ alkenyl, substituted or unsubstituted $C_2$-$C_6$ alkynyl, substituted or unsubstituted aryl, substituted or unsubstituted heteroaryl, substituted or unsubstituted silyl, substituted or unsubstituted sulfonyl, substituted or unsubstituted sulfone, substituted or unsubstituted sulfoxide, or substituted or unsubstituted thiol.

Additional aspects and advantages of the disclosure will be set forth, in part, in the detailed description and any claims which follow, and in part will be derived from the detailed description or can be learned by practice of the various aspects of the disclosure. The advantages described below will be realized and attained by means of the elements and combinations particularly pointed out in the appended claims. It is to be understood that both the foregoing general description and the following detailed description are exemplary and explanatory only and are not restrictive of the disclosure.

DETAILED DESCRIPTION

The following description of the disclosure is provided as an enabling teaching of the disclosure in its best, currently known embodiment(s). To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

General Definitions

The term "subject" refers to any individual who is the target of administration or treatment. The subject can be a vertebrate, for example, a mammal. Thus, the subject can be a human or veterinary patient. The term "patient" refers to a subject that is under the care of a treating clinician (e.g., physician).

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A^n$ is used herein as merely a generic substituent in the definitions below.

The term "alkoxy" as used herein is an alkyl group bound through a single, terminal ether linkage; that is, an "alkoxy" group can be defined as —$OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

"Aryl", as used herein, refers to 5-, 6- and 7-membered aromatic rings. The ring can be a carbocyclic, heterocyclic, fused carbocyclic, fused heterocyclic, bicarbocyclic, or biheterocyclic ring system, optionally substituted as described above for alkyl. Broadly defined, "Ar", as used herein, includes 5-, 6- and 7-membered single-ring aromatic groups that can include from zero to four heteroatoms. Examples include, but are not limited to, benzene, pyrrole, furan, thiophene, imidazole, oxazole, thiazole, triazole, pyrazole, pyridine, pyrazine, pyridazine and pyrimidine. Those aryl groups having heteroatoms in the ring structure can also be referred to as "heteroaryl", "aryl heterocycles", or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, and —CN. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles, or both rings are aromatic.

"Alkylaryl" or "aryl-alkyl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, containing carbon and one to four heteroatoms each selected from non-peroxide oxygen, sulfur, and N(Y) wherein Y is absent or is H, O, ($C_{14}$) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms containing carbon and 1, 2, 3, or 4 heteroatoms each selected from non-peroxide oxygen, sulfur, and N(Y) where Y is absent or is H, O, ($C_1$-$C_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl include, but are not limited to, furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C═O.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The terms "amine" and "amino" are art-recognized and refer to both unsubstituted and substituted amines, e.g., a moiety that can be represented by the general formula: —$NR_9R_{10}$ or $NR_9R_{10}R'_{10}$, wherein $R_9$, $R_{10}$, and $R'_{10}$ each independently represent a hydrogen, an alkyl, an alkenyl, —$(CH_2)_m$—$R'_8$ or $R_9$ and $R_{10}$ taken together with the N atom to which they are attached complete a heterocycle having from 4 to 8 atoms in the ring structure; $R'_8$ represents an aryl, a cycloalkyl, a cycloalkenyl, a heterocycle or a polycycle; and m is zero or an integer in the range of 1 to 8. In some embodiments, only one of $R_9$ or $R_{10}$ can be a carbonyl, e.g., $R_9$, $R_{10}$ and the nitrogen together do not form an imide. In some embodiments, the term "amine" does not encompass amides, e.g., wherein one of $R_9$ and $R_{10}$ represents a carbonyl. In some embodiments, $R_9$ and $R_{10}$ (and optionally $R'_{10}$) each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of $R_9$ and $R_{10}$ is an alkyl group.

The term "amide" is art-recognized as an amino-substituted carbonyl and includes a moiety that can be represented by the general formula —$CONR_9R_{10}$ wherein $R_9$ and $R_{10}$ are as defined above.

"Halogen", as used herein, refers to fluorine, chlorine, bromine, or iodine.

The term "carboxylic acid" as used herein is represented by the formula —C(O)OH. A "carboxylate" as used herein is represented by the formula —C(O)O—.

The term "ester" as used herein is represented by the formula —OC(O)$A^1$ or —C(O)O$A^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —$NO_2$.

The term "cyano" as used herein is represented by the formula —CN

The term "azido" as used herein is represented by the formula —$N_3$.

The term "sulfonyl" is used herein to refer to the sulfo-oxo group represented by the formula —$S(O)_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH_2$.

The term "thiol" or "thio" as used herein is represented by the formula —SH.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aryloxy, substituted aryloxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples and FIGURES. A number of embodiments of the invention have been described. Nevertheless, it will be understood that various modifications may be made without departing from the spirit and scope of the invention. Accordingly, other embodiments are within the scope of the following claims.

Compositions

It is understood that the compounds of the present disclosure can be used in combination with the various compositions, methods, products, and applications disclosed herein.

Activated redox-sensitive inflammasomes can drive caspase-1-dependent pyroptotic cell death, inflammatory cytokine generation, and clonal expansion. Inflammasome components can be induced by danger-associated molecular pattern (DAMP) engagement of membrane Toll-like receptors (TLR), whereas cytoplasmic complex assembly is triggered by DAMP interaction with NOD-like receptor proteins (NLRP). Once activated, inflammasomes serve as platforms for caspase-1 activation, IL-1β and IL-18 maturation, cation channel activation and pyroptosis. Neutralization of S100A9 in bone marrow plasma or pharmacologic inhibition of the NLRP3 inflammasome can suppress pyroptosis and reactive oxygen species (ROS).

The disclosure herein addresses needs in the art by providing for small molecules which can inhibit inflammasome formation. Such small molecules are useful at least for treating inflammatory diseases.

In some aspects, the compound can have a structure defined by Formula I or is a derivative thereof:

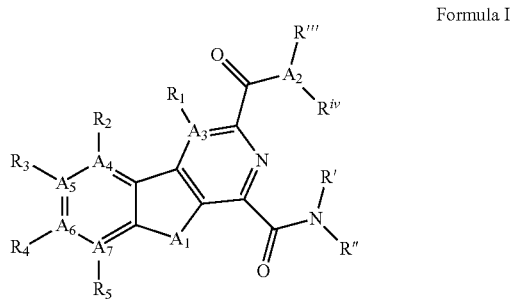

Formula I wherein $A_1$ is selected from O, $CH_2$, S, or NH;

$A_2$ is selected from O or N, wherein when $A_2$ is selected from O then $R^{iv}$ is absent;

$A_3$, $A_4$, $A^5$, $A_6$, or $A_7$ are independently selected from C, S, N;

R' and R" are independently selected from hydrogen; hydroxyl, substituted or unsubstituted $C_1$-$C_6$ alkyl, substituted or unsubstituted aminoalkyl, substituted or unsubstituted $C_1$-$C_6$ haloalkyl, substituted or unsubstituted cycloalkyl, substituted or unsubstituted cycloheteroalkyl, substituted or unsubstituted alkoxy, substituted or unsubstituted alkenyl, substituted or unsubstituted alkynyl, substituted or unsubstituted aryl, substituted or unsubstituted heteroaryl, or both R' and R" combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached;

R''' and $R^{iv}$ are independently selected from hydrogen; hydroxyl, substituted or unsubstituted $C_1$-$C_6$ alkyl, substituted or unsubstituted aminoalkyl, substituted or unsubstituted $C_1$-$C_6$ haloalkyl, substituted or unsubstituted cycloalkyl, substituted or unsubstituted cycloheteroalkyl, substituted or unsubstituted alkoxy, substituted or unsubstituted alkenyl, substituted or unsubstituted alkynyl, substituted or unsubstituted aryl, substituted or unsubstituted heteroaryl, or both R''' and $R^{iv}$ combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached;

$R_1$ is null or selected from hydrogen; hydroxyl, halide, substituted or unsubstituted nitrile, substituted or unsubstituted nitro, substituted or unsubstituted amine, substituted or unsubstituted alkyl halide, substituted or unsubstituted carboxyl, substituted or unsubstituted amide, substituted or unsubstituted ester, substituted or unsubstituted ether, substituted or unsubstituted ketone, substituted or unsubstituted $C_1$-$C_6$ alkyl, substituted or unsubstituted alkoxy, substituted or unsubstituted $C_2$-$C_6$ alkenyl, substituted or unsubstituted $C_2$-$C_6$ alkynyl, substituted or unsubstituted aryl, substituted or unsubstituted heteroaryl, substituted or unsubstituted silyl, substituted or unsubstituted sulfonyl, substituted or unsubstituted sulfone, substituted or unsubstituted sulfoxide, or substituted or unsubstituted thiol; and $R_2$-$R_5$ are independently null or independently selected from hydrogen; hydroxyl, halide, substituted or unsubstituted nitrile, substituted or unsubstituted nitro, substituted or unsubstituted amine, substituted or unsubstituted alkyl halide, substituted or unsubstituted carboxyl, substituted or unsubstituted amide, substituted or unsubstituted ester, substituted or unsubstituted ether, substituted or unsubstituted ketone, substituted or unsubstituted $C_1$-$C_6$ alkyl, substituted or unsubstituted alkoxy, substituted or unsubstituted $C_2$-$C_6$ alkenyl, substituted or unsubstituted $C_2$-$C_6$ alkynyl, substituted or unsubstituted aryl, substituted or unsubstituted heteroaryl, substituted or unsubstituted silyl, substituted or unsubstituted sulfonyl, substituted or unsubstituted sulfone, substituted or unsubstituted sulfoxide, or substituted or unsubstituted thiol.

In some embodiments of Formula I, the compound can have a structure defined by Formula I-A or a derivative thereof:

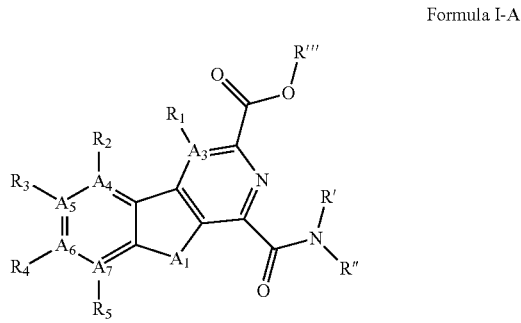

Formula I-A wherein $A_1$ is selected from O or NH;
$A_3$, $A_4$, $A_5$, $A_6$, or $A_7$ are independently selected from C, S, N;
R' and R" are independently selected from hydrogen; hydroxyl, substituted or unsubstituted $C_1$-$C_6$ alkyl, substituted or unsubstituted aminoalkyl, substituted or unsubstituted $C_1$-$C_6$ haloalkyl, substituted or unsubstituted cycloalkyl, substituted or unsubstituted cycloheteroalkyl, substituted or unsubstituted alkoxy, substituted or unsubstituted alkenyl, substituted or unsubstituted alkynyl, substituted or unsubstituted aryl, substituted or unsubstituted heteroaryl, or both R' and R" combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached;
R''' is selected from hydrogen; hydroxyl, substituted or unsubstituted $C_1$ or $C_3$-$C_6$ alkyl, substituted or unsubstituted aminoalkyl, substituted or unsubstituted $C_1$-$C_6$ haloalkyl, substituted or unsubstituted cycloalkyl, substituted or unsubstituted cycloheteroalkyl, substituted or unsubstituted alkoxy, substituted or unsubstituted alkenyl, substituted or unsubstituted alkynyl, substituted or unsubstituted aryl, substituted or unsubstituted heteroaryl;
$R^1$ is null or selected from hydrogen; hydroxyl, halide, substituted or unsubstituted nitrile, substituted or unsubstituted nitro, substituted or unsubstituted amine, substituted or unsubstituted alkyl halide, substituted or unsubstituted carboxyl, substituted or unsubstituted amide, substituted or unsubstituted ester, substituted or unsubstituted ether, substituted or unsubstituted ketone, substituted or unsubstituted $C_1$-$C_6$ alkyl, substituted or unsubstituted alkoxy, substituted or unsubstituted $C_2$-$C_6$ alkenyl, substituted or unsubstituted $C_2$-$C_6$ alkynyl, substituted or unsubstituted aryl, substituted or unsubstituted heteroaryl, substituted or unsubstituted silyl, substituted or unsubstituted sulfonyl, substituted or unsubstituted sulfone, substituted or unsubstituted sulfoxide, or substituted or unsubstituted thiol; and
$R_2$-$R_5$ are independently null or independently selected from hydrogen; hydroxyl, halide, substituted or unsubstituted nitrile, substituted or unsubstituted nitro, substituted or unsubstituted amine, substituted or unsubstituted alkyl halide, substituted or unsubstituted carboxyl, substituted or unsubstituted amide, substituted or unsubstituted ester, substituted or unsubstituted ether, substituted or unsubstituted ketone, substituted or unsubstituted $C_1$-$C_6$ alkyl, substituted or unsubstituted alkoxy, substituted or unsubstituted $C_2$-$C_6$ alkenyl, substituted or unsubstituted $C_2$-$C_6$ alkynyl, substituted or unsubstituted aryl, substituted or unsubstituted heteroaryl, substituted or unsubstituted silyl, substituted or unsubstituted sulfonyl, substituted or unsubstituted sulfone, substituted or unsubstituted sulfoxide, or substituted or unsubstituted thiol.

In some embodiments of Formula I, the compound can have a structure defined by Formula I-A-1 or a derivative thereof:

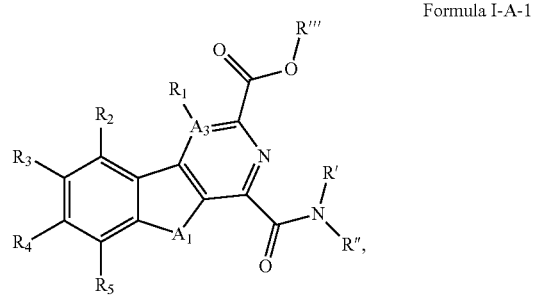

Formula I-A-1 wherein $A_1$ is selected from O or NH;
$A_3$ is selected from C, S, N;
R' and R" are independently selected from hydrogen; hydroxyl, substituted or unsubstituted $C_1$-$C_6$ alkyl, substituted or unsubstituted aminoalkyl, substituted or unsubstituted $C_1$-$C_6$ haloalkyl, substituted or unsubstituted cycloalkyl, substituted or unsubstituted cycloheteroalkyl, substituted or unsubstituted alkoxy, substituted or unsubstituted alkenyl, substituted or unsubstituted alkynyl, substituted or unsubstituted aryl, substituted or unsubstituted heteroaryl, or both R' and R" combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached;
R''' is selected from hydrogen; hydroxyl, substituted or unsubstituted $C_1$ or $C_3$-$C_6$ alkyl, substituted or unsubstituted aminoalkyl, substituted or unsubstituted $C_1$-$C_6$ haloalkyl, substituted or unsubstituted cycloalkyl, substituted or unsubstituted cycloheteroalkyl, substituted or unsubstituted alkoxy, substituted or unsubstituted alkenyl, substituted or unsubstituted alkynyl, substituted or unsubstituted aryl, substituted or unsubstituted heteroaryl;
$R_1$ is null or selected from hydrogen; hydroxyl, halide, substituted or unsubstituted nitrile, substituted or unsubstituted nitro, substituted or unsubstituted amine, substituted or unsubstituted alkyl halide, substituted or unsubstituted carboxyl, substituted or unsubstituted amide, substituted or unsubstituted ester, substituted or unsubstituted ether, substituted or unsubstituted ketone, substituted or unsubstituted $C_1$-$C_6$ alkyl, substituted or unsubstituted alkoxy, substituted or unsubstituted $C_2$-$C_6$ alkenyl, substituted or unsubstituted $C_2$-$C_6$ alkynyl, substituted or unsubstituted aryl, substituted or unsubstituted heteroaryl, substituted or unsubstituted silyl, substituted or unsubstituted sulfonyl, substituted or unsubstituted sulfone, substituted or unsubstituted sulfoxide, or substituted or unsubstituted thiol; and $R_2$-$R_5$ are independently null or independently selected from hydrogen; hydroxyl, halide, substituted or unsubstituted nitrile, substituted or unsubstituted nitro, substituted or unsubstituted amine, substituted or unsubstituted alkyl halide, substituted or unsubstituted carboxyl, substituted or unsubstituted amide, substituted or unsubstituted ester, substituted or unsubstituted ether, substituted or unsubstituted ketone, substituted or unsubstituted $C_1$-$C_6$ alkyl, substituted or unsubstituted alkoxy, substituted or unsubstituted $C_2$-$C_6$ alkenyl, substituted or unsubstituted $C_2$-$C_6$ alkynyl, substituted or unsubstituted aryl, substituted or unsubstituted heteroaryl, substituted or unsubstituted silyl, substituted or unsubstituted sulfonyl, substituted or unsubstituted sulfone, substituted or unsubstituted sulfoxide, or substituted or unsubstituted thiol.

In some embodiments of Formula I, the compound can have a structure defined by Formula I-A-2 or a derivative thereof:

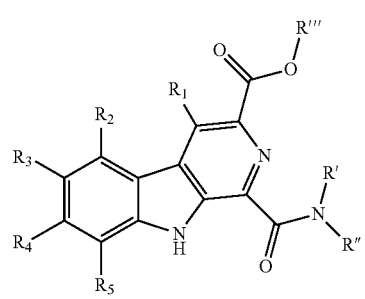

Formula I-A-2 wherein R' and R" are independently selected from hydrogen; hydroxyl, substituted or unsubstituted $C_1$-$C_6$ alkyl, substituted or unsubstituted aminoalkyl, substituted or unsubstituted $C_1$-$C_6$ haloalkyl, substituted or unsubstituted cycloalkyl, substituted or unsubstituted cycloheteroalkyl, substituted or unsubstituted alkoxy, substituted or unsubstituted alkenyl, substituted or unsubstituted alkynyl, substituted or unsubstituted aryl, substituted or unsubstituted heteroaryl, or both R' and R" combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached;

R''' is selected from hydrogen; hydroxyl, substituted or unsubstituted $C_1$ or $C_3$-$C_6$ alkyl, substituted or unsubstituted aminoalkyl, substituted or unsubstituted $C_1$-$C_6$ haloalkyl, substituted or unsubstituted cycloalkyl, substituted or unsubstituted cycloheteroalkyl, substituted or unsubstituted alkoxy, substituted or unsubstituted alkenyl, substituted or unsubstituted alkynyl, substituted or unsubstituted aryl, substituted or unsubstituted heteroaryl;

$R_1$ is null or selected from hydrogen; hydroxyl, halide, substituted or unsubstituted nitrile, substituted or unsubstituted nitro, substituted or unsubstituted amine, substituted or unsubstituted alkyl halide, substituted or unsubstituted carboxyl, substituted or unsubstituted amide, substituted or unsubstituted ester, substituted or unsubstituted ether, substituted or unsubstituted ketone, substituted or unsubstituted $C_1$-$C_6$ alkyl, substituted or unsubstituted alkoxy, substituted or unsubstituted $C_2$-$C_6$ alkenyl, substituted or unsubstituted $C_2$-$C_6$ alkynyl, substituted or unsubstituted aryl, substituted or unsubstituted heteroaryl, substituted or unsubstituted silyl, substituted or unsubstituted sulfonyl, substituted or unsubstituted sulfone, substituted or unsubstituted sulfoxide, or substituted or unsubstituted thiol; and $R_2$-$R_5$ are independently null or independently selected from hydrogen; hydroxyl, halide, substituted or unsubstituted nitrile, substituted or unsubstituted nitro, substituted or unsubstituted amine, substituted or unsubstituted alkyl halide, substituted or unsubstituted carboxyl, substituted or unsubstituted amide, substituted or unsubstituted ester, substituted or unsubstituted ether, substituted or unsubstituted ketone, substituted or unsubstituted $C_1$-$C_6$ alkyl, substituted or unsubstituted alkoxy, substituted or unsubstituted $C_2$-$C_6$ alkenyl, substituted or unsubstituted $C_2$-$C_6$ alkynyl, substituted or unsubstituted aryl, substituted or unsubstituted heteroaryl, substituted or unsubstituted silyl, substituted or unsubstituted sulfonyl, substituted or unsubstituted sulfone, substituted or unsubstituted sulfoxide, or substituted or unsubstituted thiol.

In some embodiments of Formula I, the compound can have a structure defined by Formula I-B or a derivative thereof:

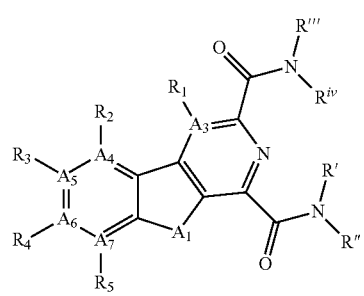

Formula I-B wherein $A_1$ is selected from O or NH;

$A_3$, $A_4$, $A_5$, $A_6$, or $A_7$ are independently selected from C, S, or N;

R' and R" are independently selected from hydrogen; hydroxyl, substituted or unsubstituted $C_1$-$C_6$ alkyl, substituted or unsubstituted aminoalkyl, substituted or unsubstituted $C_1$-$C_6$ haloalkyl, substituted or unsubstituted cycloalkyl, substituted or unsubstituted cycloheteroalkyl, substituted or unsubstituted alkoxy, substituted or unsubstituted alkenyl, substituted or unsubstituted alkynyl, substituted or unsubstituted aryl, substituted or unsubstituted heteroaryl, or both R' and R" combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached;

R''' and $R^{iv}$ are independently selected from hydrogen; hydroxyl, substituted or unsubstituted $C_1$-$C_6$ alkyl, substituted or unsubstituted aminoalkyl, substituted or unsubstituted $C_1$-$C_6$ haloalkyl, substituted or unsubstituted cycloalkyl, substituted or unsubstituted cycloheteroalkyl, substituted or unsubstituted alkoxy, substituted or unsubstituted alkenyl, substituted or unsubstituted alkynyl, substituted or unsubstituted aryl, substituted or unsubstituted heteroaryl, or both R''' and $R^{iv}$ combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached;

$R_1$ is null or selected from hydrogen; hydroxyl, halide, substituted or unsubstituted nitrile, substituted or unsubstituted nitro, substituted or unsubstituted amine, substituted or unsubstituted alkyl halide, substituted or unsubstituted carboxyl, substituted or unsubstituted amide, substituted or unsubstituted ester, substituted or unsubstituted ether, substituted or unsubstituted ketone, substituted or unsubstituted $C_1$-$C_6$ alkyl, substituted or unsubstituted alkoxy, substituted or unsubstituted $C_2$-$C_6$ alkenyl, substituted or unsubstituted $C_2$-$C_6$ alkynyl, substituted or unsubstituted aryl, substituted or unsubstituted heteroaryl, substituted or unsubstituted silyl, substituted or unsubstituted sulfonyl, substituted or unsubstituted sulfone, substituted or unsubstituted sulfoxide, or substituted or unsubstituted thiol; and $R_2$-$R_5$ are independently null or independently selected from hydrogen; hydroxyl, halide, substituted or unsubstituted nitrile, substituted or unsubstituted nitro, substituted or unsubstituted amine, substituted or unsubstituted alkyl halide, substituted or unsubstituted carboxyl, substituted or unsubstituted amide, substituted or unsubstituted ester, substituted or unsubstituted ether, substituted or unsubstituted ketone, substituted or unsubstituted $C_1$-$C_6$ alkyl, substituted or unsubstituted alkoxy, substituted or unsubstituted $C_2$-$C_6$ alkenyl, substituted or unsubstituted $C_2$-$C_6$ alkynyl, substituted or unsubstituted aryl, substituted or unsubstituted heteroaryl, substituted or unsubstituted silyl, substituted or unsubstituted sulfonyl, substituted or unsubstituted sulfone, substituted or unsubstituted sulfoxide, or substituted or unsubstituted thiol.

In some embodiments of Formula I, the compound can have a structure defined by Formula I-B-1 or a derivative thereof:

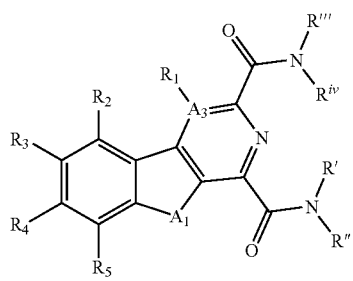

Formula I-B-1 wherein $A_1$ is selected from O or NH;
$A_3$ is selected from C, S, or N;
R' and R'' are independently selected from hydrogen; hydroxyl, substituted or unsubstituted $C_1$-$C_6$ alkyl, substituted or unsubstituted aminoalkyl, substituted or unsubstituted $C_1$-$C_6$ haloalkyl, substituted or unsubstituted cycloalkyl, substituted or unsubstituted cycloheteroalkyl, substituted or unsubstituted alkoxy, substituted or unsubstituted alkenyl, substituted or unsubstituted alkynyl, substituted or unsubstituted aryl, substituted or unsubstituted heteroaryl, or both R' and R'' combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached;

R''' and $R^{iv}$ are independently selected from hydrogen; hydroxyl, substituted or unsubstituted $C_1$-$C_6$ alkyl, substituted or unsubstituted aminoalkyl, substituted or unsubstituted $C_1$-$C_6$ haloalkyl, substituted or unsubstituted cycloalkyl, substituted or unsubstituted cycloheteroalkyl, substituted or unsubstituted alkoxy, substituted or unsubstituted alkenyl, substituted or unsubstituted alkynyl, substituted or unsubstituted aryl, substituted or unsubstituted heteroaryl, or both R''' and $R^{iv}$ combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached;

$R_1$ is null or selected from hydrogen; hydroxyl, halide, substituted or unsubstituted nitrile, substituted or unsubstituted nitro, substituted or unsubstituted amine, substituted or unsubstituted alkyl halide, substituted or unsubstituted carboxyl, substituted or unsubstituted amide, substituted or unsubstituted ester, substituted or unsubstituted ether, substituted or unsubstituted ketone, substituted or unsubstituted $C_1$-$C_6$ alkyl, substituted or unsubstituted alkoxy, substituted or unsubstituted $C_2$-$C_6$ alkenyl, substituted or unsubstituted $C_2$-$C_6$ alkynyl, substituted or unsubstituted aryl, substituted or unsubstituted heteroaryl, substituted or unsubstituted silyl, substituted or unsubstituted sulfonyl, substituted or unsubstituted sulfone, substituted or unsubstituted sulfoxide, or substituted or unsubstituted thiol; and $R_2$-$R_5$ are independently null or independently selected from hydrogen; hydroxyl, halide, substituted or unsubstituted nitrile, substituted or unsubstituted nitro, substituted or unsubstituted amine, substituted or unsubstituted alkyl halide, substituted or unsubstituted carboxyl, substituted or unsubstituted amide, substituted or unsubstituted ester, substituted or unsubstituted ether, substituted or unsubstituted ketone, substituted or unsubstituted $C_1$-$C_6$ alkyl, substituted or unsubstituted alkoxy, substituted or unsubstituted $C_2$-$C_6$ alkenyl, substituted or unsubstituted $C_2$-$C_6$ alkynyl, substituted or unsubstituted aryl, substituted or unsubstituted heteroaryl, substituted or unsubstituted silyl, substituted or unsubstituted sulfonyl, substituted or unsubstituted sulfone, substituted or unsubstituted sulfoxide, or substituted or unsubstituted thiol.

In some embodiments of Formula I, the compound can have a structure defined by Formula I-B-2 or a derivative thereof:

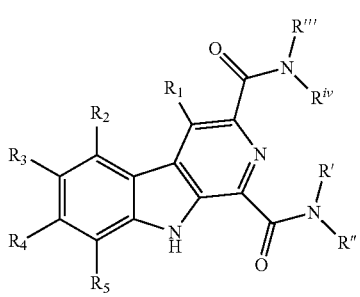

Formula I-B-2 wherein R' and R" are independently selected from hydrogen; hydroxyl, substituted or unsubstituted $C_1$-$C_6$ alkyl, substituted or unsubstituted aminoalkyl, substituted or unsubstituted $C_1$-$C_6$ haloalkyl, substituted or unsubstituted cycloalkyl, substituted or unsubstituted cycloheteroalkyl, substituted or unsubstituted alkoxy, substituted or unsubstituted alkenyl, substituted or unsubstituted alkynyl, substituted or unsubstituted aryl, substituted or unsubstituted heteroaryl, or both R' and R" combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached;

R''' and $R^{iv}$ are independently selected from hydrogen; hydroxyl, substituted or unsubstituted $C_1$-$C_6$ alkyl, substituted or unsubstituted aminoalkyl, substituted or unsubstituted $C_1$-$C_6$ haloalkyl, substituted or unsubstituted cycloalkyl, substituted or unsubstituted cycloheteroalkyl, substituted or unsubstituted alkoxy, substituted or unsubstituted alkenyl, substituted or unsubstituted alkynyl, substituted or unsubstituted aryl, substituted or unsubstituted heteroaryl, or both R''' and $R^{iv}$ combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached;

$R_1$ is null or selected from hydrogen; hydroxyl, halide, substituted or unsubstituted nitrile, substituted or unsubstituted nitro, substituted or unsubstituted amine, substituted or unsubstituted alkyl halide, substituted or unsubstituted carboxyl, substituted or unsubstituted amide, substituted or unsubstituted ester, substituted or unsubstituted ether, substituted or unsubstituted ketone, substituted or unsubstituted $C_1$-$C_6$ alkyl, substituted or unsubstituted alkoxy, substituted or unsubstituted $C_2$-$C_6$ alkenyl, substituted or unsubstituted $C_2$-$C_6$ alkynyl, substituted or unsubstituted aryl, substituted or unsubstituted heteroaryl, substituted or unsubstituted silyl, substituted or unsubstituted sulfonyl, substituted or unsubstituted sulfone, substituted or unsubstituted sulfoxide, or substituted or unsubstituted thiol; and $R_2$-$R_5$ are independently null or independently selected from hydrogen; hydroxyl, halide, substituted or unsubstituted nitrile, substituted or unsubstituted nitro, substituted or unsubstituted amine, substituted or unsubstituted alkyl halide, substituted or unsubstituted carboxyl, substituted or unsubstituted amide, substituted or unsubstituted ester, substituted or unsubstituted ether, substituted or unsubstituted ketone, substituted or unsubstituted $C_1$-$C_6$ alkyl, substituted or unsubstituted alkoxy, substituted or unsubstituted $C_2$-$C_6$ alkenyl, substituted or unsubstituted $C_2$-$C_6$ alkynyl, substituted or unsubstituted aryl, substituted or unsubstituted heteroaryl, substituted or unsubstituted silyl, substituted or unsubstituted sulfonyl, substituted or unsubstituted sulfone, substituted or unsubstituted sulfoxide, or substituted or unsubstituted thiol.

In some embodiments of Formula I, Formula I-A, Formula I-A-1, Formula I-A-2, Formula I-B, Formula I-B-1, Formula I-B-2, or a derivative thereof, $A_1$ is NH.

In some embodiments of Formula I, Formula I-A, Formula I-A-1, Formula I-A-2, Formula I-B, Formula I-B-1, Formula I-B-2, or a derivative thereof, $A_3$ is selected from C or N. In some embodiments, $A_3$ can be C. In some embodiments, $A_3$ can be N.

In some embodiments of Formula I, Formula I-A, Formula I-A-1, Formula I-A-2, Formula I-B, Formula I-B-1, Formula I-B-2, or a derivative thereof, $A_4$ is selected from C or N. In some embodiments, $A_4$ can be C. In some embodiments, $A_4$ can be N.

In some embodiments of Formula I, Formula I-A, Formula I-A-1, Formula I-A-2, Formula I-B, Formula I-B-1, Formula I-B-2, or a derivative thereof, $A_5$ is selected from C or N. In some embodiments, $A_5$ can be C. In some embodiments, $A_5$ can be N.

In some embodiments of Formula I, Formula I-A, Formula I-A-1, Formula I-A-2, Formula I-B, Formula I-B-1, Formula I-B-2, or a derivative thereof, $A_6$ is selected from C or N. In some embodiments, $A_6$ can be C. In some embodiments, $A_6$ can be N.

In some embodiments of Formula I, Formula I-A, Formula I-A-1, Formula I-A-2, Formula I-B, Formula I-B-1, Formula I-B-2, or a derivative thereof, $A_7$ is selected from C or N. In some embodiments, $A_7$ can be C. In some embodiments, $A_7$ can be N.

In some embodiments of Formula I, Formula I-A, Formula I-A-1, Formula I-A-2, Formula I-B, Formula I-B-1, Formula I-B-2, or a derivative thereof, $A_4$, $A_5$, $A_6$, or $A_7$ are all C. In some embodiments of Formula I, Formula I-A, Formula I-A-1, Formula I-A-2, Formula I-B, Formula I-B-1, Formula I-B-2, or a derivative thereof, $A_3$, $A_4$, $A_5$, $A_6$, or $A_7$ are all C.

In some embodiments of Formula I, Formula I-A, Formula I-A-1, Formula I-A-2, Formula I-B, Formula I-B-1, Formula I-B-2, or a derivative thereof, R' is selected from hydrogen; unsubstituted $C_1$-$C_6$ alkyl, unsubstituted aminoalkyl, unsubstituted $C_1$-$C_6$ haloalkyl, unsubstituted alkoxy, substituted or unsubstituted cycloalkyl, substituted or unsubstituted cycloheteroalkyl, substituted or unsubstituted aryl, substituted or unsubstituted heteroaryl, or both R' and R" combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached. In some embodiments, R' is selected from hydrogen; unsubstituted $C_1$-$C_6$ alkyl, unsubstituted $C_1$-$C_6$ haloalkyl, alkoxy, or both R' and R" combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached.

In some embodiments of Formula I, Formula I-A, Formula I-A-1, Formula I-A-2, Formula I-B, Formula I-B-1, Formula I-B-2, or a derivative thereof, R" is selected from hydrogen; unsubstituted $C_1$-$C_6$ alkyl, unsubstituted aminoalkyl, unsubstituted $C_1$-$C_6$ haloalkyl, unsubstituted alkoxy, substituted or unsubstituted cycloalkyl, substituted or unsubstituted cycloheteroalkyl, substituted or unsubstituted aryl, substituted or unsubstituted heteroaryl, or both R' and R" combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached. In some embodiments, R" is selected from hydrogen; unsubstituted $C_1$-$C_6$ alkyl, unsubstituted $C_1$-$C_6$ haloalkyl, unsubstituted alkoxy, or both R' and R" combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached.

In some embodiments of Formula I, Formula I-A, Formula I-A-1, Formula I-A-2, Formula I-B, Formula I-B-1, Formula I-B-2, or a derivative thereof, R' and R" are independently selected from hydrogen; unsubstituted $C_1$-$C_6$ alkyl, unsubstituted aminoalkyl, unsubstituted $C_1$-$C_6$ haloalkyl, unsubstituted alkoxy, substituted or unsubstituted cycloalkyl, substituted or unsubstituted cycloheteroalkyl, substituted or unsubstituted aryl, substituted or unsubstituted heteroaryl, or both R' and R" combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached. In some embodiments, R' and R" are independently selected from hydrogen; unsubstituted $C_1$-$C_6$ alkyl, unsubstituted $C_1$-$C_6$ haloalkyl, unsubstituted alkoxy, or both R' and R" combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached. In some embodiments, R' and R" are the same. In some embodiments, R' and R" are different.

In some embodiments of Formula I, Formula I-A, Formula I-A-1, Formula I-A-2, Formula I-B, Formula I-B-1, Formula I-B-2, or a derivative thereof, R'" and $R^{iv}$ are independently selected from hydrogen; substituted or unsubstituted $C_1$-$C_6$ alkyl, substituted or unsubstituted aminoalkyl, substituted or unsubstituted $C_1$-$C_6$ haloalkyl, substituted or unsubstituted alkoxy, substituted or unsubstituted cycloalkyl, substituted or unsubstituted cycloheteroalkyl, substituted or unsubstituted aryl, substituted or unsubstituted heteroaryl, or both R'" and $R^{iv}$ combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached. In some embodiments, R'" is hydrogen and $R^{iv}$ is independently selected from hydrogen; substituted or unsubstituted $C_1$-$C_6$ alkyl, substituted or unsubstituted aminoalkyl, substituted or unsubstituted $C_1$-$C_6$ haloalkyl, substituted or unsubstituted alkoxy, substituted or unsubstituted cycloalkyl, substituted or unsubstituted cycloheteroalkyl, substituted or unsubstituted aryl, substituted or unsubstituted heteroaryl, or both R'" and $R^{iv}$ combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached. In some embodiments, R'" is hydrogen and $R^{iv}$ is independently selected from substituted or unsubstituted $C_1$-$C_6$ alkyl, substituted or unsubstituted aminoalkyl, substituted or unsubstituted $C_1$-$C_6$ haloalkyl, substituted or unsubstituted alkoxy, substituted or unsubstituted cycloalkyl, substituted or unsubstituted cycloheteroalkyl, substituted or unsubstituted aryl, substituted or unsubstituted heteroaryl, or both R'" and $R^{iv}$ combine to form a substituted or unsubstituted $C_3$-$C_8$ cycloalkyl, a substituted or unsubstituted $C_3$-$C_8$ cycloalkenyl, a substituted or unsubstituted $C_2$-$C_7$ heterocycloalkyl, or a substituted or unsubstituted $C_2$-$C_7$ heterocycloalkenyl together with the atom to which they are attached. In some embodiments of Formula I, Formula I-A, Formula I-A-1, Formula I-A-2, Formula I-B, Formula I-B-1, Formula I-B-2, or a derivative thereof, R'" and $R^{iv}$ are the same. In some embodiments of Formula I, Formula I-A, Formula I-A-1, Formula I-A-2, Formula I-B, Formula I-B-1, Formula I-B-2, or a derivative thereof, R'" and $R^{iv}$ are different.

In some embodiments of Formula I, Formula I-A, Formula I-A-1, Formula I-A-2, Formula I-B, Formula I-B-1, Formula I-B-2, or a derivative thereof, $R_1$ is selected from hydrogen; hydroxyl, halide, unsubstituted nitrile, unsubstituted nitro, unsubstituted amine, unsubstituted alkyl halide, unsubstituted carboxyl, unsubstituted amide, unsubstituted ester, unsubstituted ether, unsubstituted $C_1$-$C_6$ alkyl, unsubstituted alkoxy, unsubstituted $C_2$-$C_6$ alkenyl, substituted or unsubstituted aryl, substituted or unsubstituted heteroaryl, or unsubstituted thiol. For example, $R_1$ is selected from hydrogen; hydroxyl, halide, unsubstituted nitrile, unsubstituted nitro, unsubstituted amine, unsubstituted alkyl halide, unsubstituted $C_1$-$C_6$ alkyl, or unsubstituted thiol. In some embodiments, $R_1$ is selected from hydrogen; halide, or unsubstituted $C_1$-$C_6$ alkyl. IN some embodiments, $R_1$ is hydrogen.

In some embodiments of Formula I, Formula I-A, Formula I-A-1, Formula I-A-2, Formula I-B, Formula I-B-1, Formula I-B-2, or a derivative thereof, $R_2$ is selected from hydrogen; hydroxyl, halide, unsubstituted nitrile, unsubstituted nitro, unsubstituted amine, unsubstituted alkyl halide, unsubstituted carboxyl, unsubstituted amide, unsubstituted ester, unsubstituted ether, unsubstituted $C_1$-$C_6$ alkyl, unsubstituted alkoxy, unsubstituted $C_2$-$C_6$ alkenyl, substituted or unsubstituted aryl, substituted or unsubstituted heteroaryl, or unsubstituted thiol. For example, $R_2$ is selected from hydrogen; hydroxyl, halide, unsubstituted nitrile, unsubstituted nitro, unsubstituted amine, unsubstituted alkyl halide, unsubstituted $C_1$-$C_6$ alkyl, or unsubstituted thiol. In some embodiments, $R_2$ is selected from hydrogen; halide, or unsubstituted $C_1$-$C_6$ alkyl. In some embodiments, $R_2$ is hydrogen.

In some embodiments of Formula I, Formula I-A, Formula I-A-1, Formula I-A-2, Formula I-B, Formula I-B-1, Formula I-B-2, or a derivative thereof, $R_3$ is selected from hydrogen; hydroxyl, halide, unsubstituted nitrile, unsubstituted nitro, unsubstituted amine, unsubstituted alkyl halide, unsubstituted carboxyl, unsubstituted amide, unsubstituted ester, unsubstituted ether, unsubstituted $C_1$-$C_6$ alkyl, unsubstituted alkoxy, unsubstituted $C_2$-$C_6$ alkenyl, substituted or unsubstituted aryl, substituted or unsubstituted heteroaryl, or unsubstituted thiol. For example, $R_3$ is selected from hydrogen; hydroxyl, halide, unsubstituted nitrile, unsubstituted nitro, unsubstituted amine, unsubstituted alkyl halide, unsubstituted $C_1$-$C_6$ alkyl, or unsubstituted thiol. In some embodiments, $R_3$ is selected from hydrogen; halide, or unsubstituted $C_1$-$C_6$ alkyl. In some embodiments, $R_3$ is hydrogen.

In some embodiments of Formula I, Formula I-A, Formula I-A-1, Formula I-A-2, Formula I-B, Formula I-B-1, Formula I-B-2, or a derivative thereof, $R_4$ is selected from hydrogen; hydroxyl, halide, unsubstituted nitrile, unsubstituted nitro, unsubstituted amine, unsubstituted alkyl halide, unsubstituted carboxyl, unsubstituted amide, unsubstituted ester, unsubstituted ether, unsubstituted $C_1$-$C_6$ alkyl, unsubstituted alkoxy, unsubstituted $C_2$-$C_6$ alkenyl, substituted or unsubstituted aryl, substituted or unsubstituted heteroaryl, or unsubstituted thiol. For example, $R_4$ is selected from hydrogen; hydroxyl, halide, unsubstituted nitrile, unsubstituted nitro, unsubstituted amine, unsubstituted alkyl halide, unsubstituted $C_1$-$C_6$ alkyl, or unsubstituted thiol. In some embodiments, $R_4$ is selected from hydrogen; halide, or unsubstituted $C_1$-$C_6$ alkyl. In some embodiments, $R_4$ is hydrogen.

In some embodiments of Formula I, Formula I-A, Formula I-A-1, Formula I-A-2, Formula I-B, Formula I-B-1, Formula I-B-2, or a derivative thereof, $R_5$ is selected from hydrogen; hydroxyl, halide, unsubstituted nitrile, unsubstituted nitro, unsubstituted amine, unsubstituted alkyl halide, unsubstituted carboxyl, unsubstituted amide, unsubstituted ester, unsubstituted ether, unsubstituted $C_1$-$C_6$ alkyl, unsubstituted alkoxy, unsubstituted $C_2$-$C_6$ alkenyl, substituted or unsubstituted aryl, substituted or unsubstituted heteroaryl, or unsubstituted thiol. For example, $R_5$ is selected from hydrogen; hydroxyl, halide, unsubstituted nitrile, unsubstituted nitro, unsubstituted amine, unsubstituted alkyl halide, unsubstituted $C_1$-$C_6$ alkyl, or unsubstituted thiol. In some embodiments, $R_5$ is selected from hydrogen; halide, or unsubstituted $C_1$-$C_6$ alkyl. In some embodiments, $R_5$ is hydrogen.

In some embodiments of Formula I, Formula I-A, Formula I-A-1, Formula I-A-2, Formula I-B, Formula I-B-1, Formula I-B-2, or a derivative thereof, $R_2$-$R_5$ are independently selected from hydrogen; halide, or unsubstituted $C_1$-$C_6$ alkyl. For example, $R_2$-$R_5$ are all hydrogen.

In some embodiments of Formula I, Formula I-A, Formula I-A-1, Formula I-A-2, Formula I-B, Formula I-B-1, Formula I-B-2, or a derivative thereof, the compound can have a structure according to Formula 4a-4e or Formula 6a-6x.

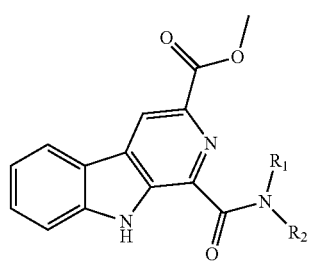

4a-e

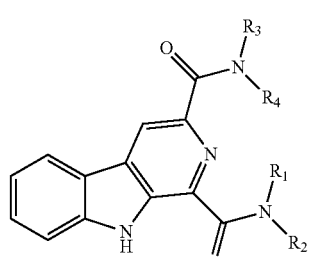

6a-x

| Compounds | $NR_1R_2$ | $NR_3R_4$ |
|---|---|---|
| 4a | $NH_2$ | — |
| 4b | 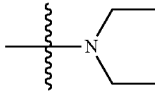 | — |
| 4c | 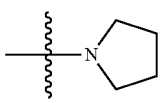 [SMILES: *N1CCCC1] | — |
| 4d | 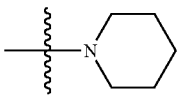 | — |
| 4e | 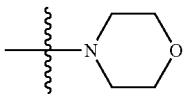 | — |
| 6a | $NH_2$ | 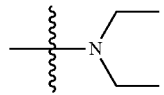 |
| 6b | $NH_2$ | 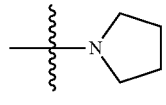 [SMILES: *N1CCCC1] |
| 6c | $NH_2$ | 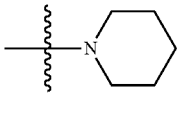 [SMILES: *N1CCCCC1] |
| 6d | $NH_2$ | 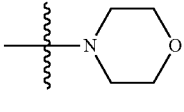 |
| 6e | $NH_2$ | 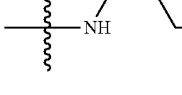 |

-continued

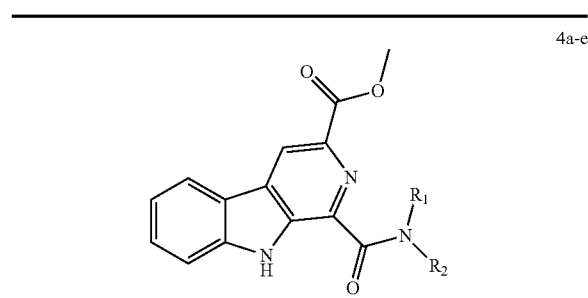
4a-e

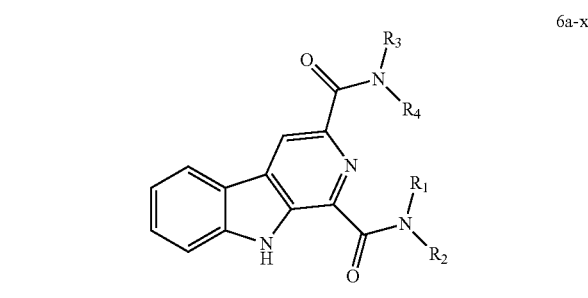
6a-x

| Compounds | NR₁R₂ | NR₃R₄ |
|---|---|---|
| 6f | NH₂ | NHEt |
| 6g | NH₂ | N(CH₃)₂ |
| 6h | NH₂ | N(CH₃)(Et) |
| 6i | NH₂ | NHtBu |
| 6j | NH₂ | NHCH₂-cyclohexyl |
| 6k | NH₂ | NHPh |
| 6l | pyrrolidinyl | piperidinyl |
| 6m | piperidinyl | piperidinyl |
| 6n | NH₂ | N(CH₃)Ph |

-continued

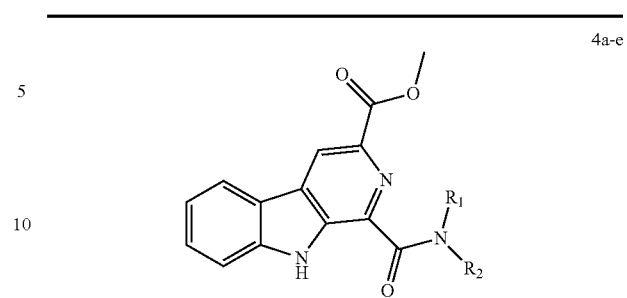
4a-e

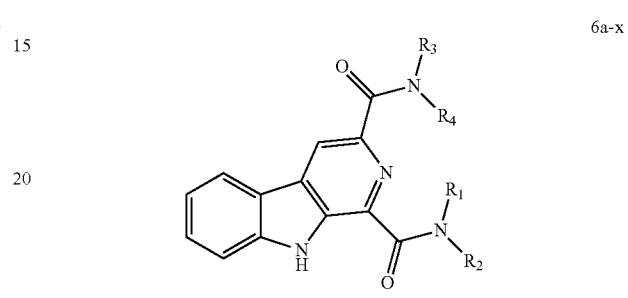
6a-x

| Compounds | NR₁R₂ | NR₃R₄ |
|---|---|---|
| 6o | NH₂ | N(CH₃)CH₂Ph |
| 6p | NH₂ | NHCH₂CH₂N(CH₃)₂ |
| 6q | NH₂ | NHCH₂CH₂CH₂-pyrrolidinyl |
| 6r | NH₂ | piperazinyl-NBoc |
| 6s | NH₂ | piperazinyl-NH |
| 6t | NH₂ | OH |
| 6u | NH₂ | octahydropyrrolo[3,4-b]pyrrole |

-continued

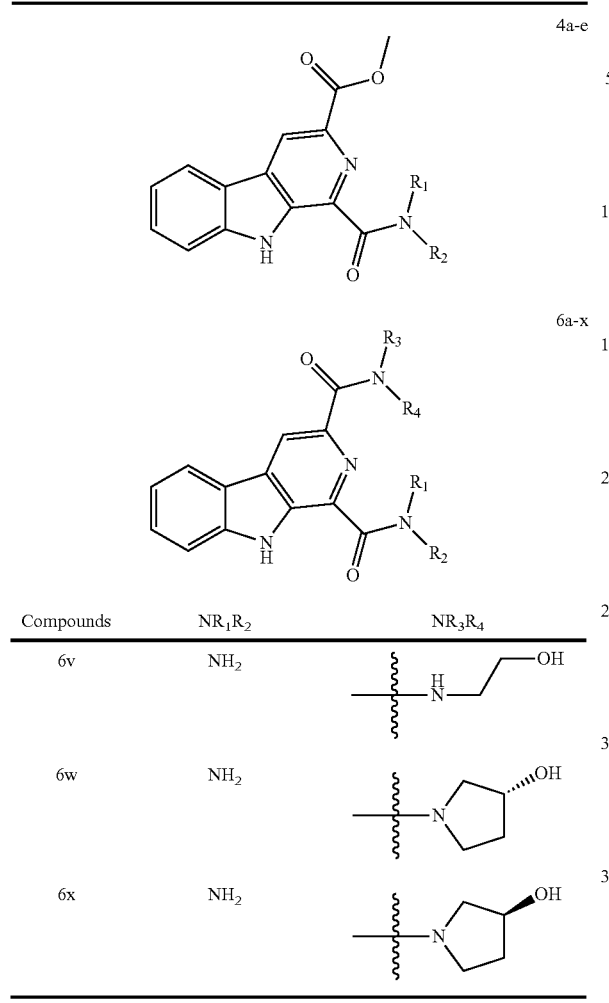

| Compounds | NR₁R₂ | NR₃R₄ |
|---|---|---|
| 6v | NH₂ | 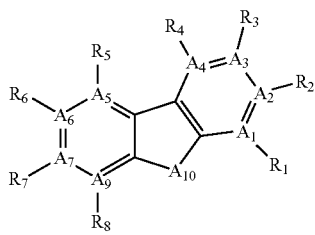 |
| 6w | NH₂ | (S)-3-hydroxypyrrolidinyl |
| 6x | NH₂ | (R)-3-hydroxypyrrolidinyl |

In some embodiments, the compound can have a structure defined by Formula II or is a derivative thereof:

Formula II wherein $A_1$-$A_{10}$ are independently selected from C, S, N; and $R_1$-$R_8$ are null or independently selected from hydrogen; hydroxyl, halide, substituted or unsubstituted nitrile, substituted or unsubstituted nitro, substituted or unsubstituted amine, substituted or unsubstituted alkyl halide, substituted or unsubstituted carboxyl, substituted or unsubstituted amide, substituted or unsubstituted ester, substituted or unsubstituted ether, substituted or unsubstituted ketone, substituted or unsubstituted with alkyl, substituted or unsubstituted alkoxy, substituted or unsubstituted alkenyl, substituted or unsubstituted alkynyl, substituted or unsubstituted aryl, substituted or unsubstituted heteroaryl, substituted or unsubstituted silyl, substituted or unsubstituted sulfonyl, substituted or unsubstituted sulfone, substituted or unsubstituted sulfoxide, or substituted or unsubstituted thiol.

In some embodiments of Formula II, the compound can have a structure below or is a

A

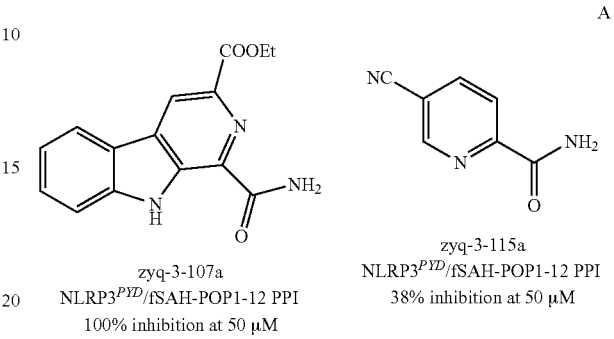

zyq-3-107a
NLRP3$^{PYD}$/fSAH-POP1-12 PPI
100% inhibition at 50 μM zyq-3-115a
NLRP3$^{PYD}$/fSAH-POP1-12 PPI
38% inhibition at 50 μM zyq-3-100b
NLRP3$^{PYD}$/fSAH-POP1-12 PPI
43% inhibition at 50 μM zyq-3-19
NLRP3$^{PYD}$/fSAH-POP1-12 PPI
41% inhibition at 50 μM derivative thereof

B 9H-pyrido-[3,4]-indole
NLRP3$^{PYD}$/fSAH-POP1-12 PPI
$K_i > 50$ μM

SC-200163
NLRP3$^{PYD}$/fSAH-POP1-12 PPI
$K_i > 50$ μM

FG7142
NLRP3$^{PYD}$/fSAH-POP1-12 PPI
$K_i > 50$ μM

Harmane
NLRP3$^{PYD}$/fSAH-POP1-12 PPI
$K_i = 22 \pm 1.7$ μM

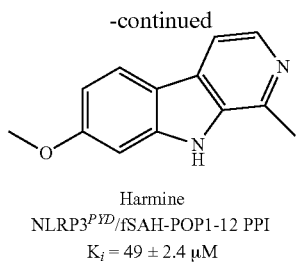

Harmine
NLRP3$^{PYD}$/fSAH-POP1-12 PPI
$K_i = 49 \pm 2.4$ μM

Also disclosed herein pharmaceutical compositions comprising a therapeutically effective amount of a pharmaceutically acceptable excipient and a compound described herein. In some embodiments, the compound is present in a therapeutically effective amount to inhibit inflammasome. Suitable excipients include, but are not limited to, salts, diluents, (e.g., Tris-HCl, acetate, phosphate), preservatives (e.g., Thimerosal, benzyl alcohol, parabens), binders, fillers, solubilizers, disintegrants, sorbents, solvents, pH modifying agents, antioxidants, antiinfective agents, suspending agents, wetting agents, viscosity modifiers, tonicity agents, stabilizing agents, and other components and combinations thereof. Suitable pharmaceutically acceptable excipients are preferably selected from materials which are generally recognized as safe (GRAS), and may be administered to an individual without causing undesirable biological side effects or unwanted interactions. Suitable excipients and their formulations are described in Remington's Pharmaceutical Sciences, 16th ed. 1980, Mack Publishing Co. In addition, such compositions can be complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Suitable dosage forms for administration, e.g., parenteral administration, include solutions, suspensions, and emulsions. Typically, the components of the formulation are dissolved or suspended in a suitable solvent such as, for example, water, Ringer's solution, phosphate buffered saline (PBS), or isotonic sodium chloride. The formulation may also be a sterile solution, suspension, or emulsion in a nontoxic, parenterally acceptable diluent or solvent such as 1,3-butanediol. In some cases, formulations can include one or more tonicity agents to adjust the isotonic range of the formulation. Suitable tonicity agents are well known in the art and include glycerin, mannitol, sorbitol, sodium chloride, and other electrolytes. In some cases, the formulations can be buffered with an effective amount of buffer necessary to maintain a pH suitable for parenteral administration. Suitable buffers are well known by those skilled in the art and some examples of useful buffers are acetate, borate, carbonate, citrate, and phosphate buffers. In some embodiments, the formulation can be distributed or packaged in a liquid form, or alternatively, as a solid, obtained, for example by lyophilization of a suitable liquid formulation, which can be reconstituted with an appropriate carrier or diluent prior to administration. The pharmaceutical compositions comprise a compound that selectively binds a nucleic acid-binding polypeptide, wherein the nucleic acid-binding polypeptide is capable of intracellular aggregation and is associated with a neurodegenerative disease in a therapeutically effective amount sufficient to treat a neurodegenerative disease. The pharmaceutical compositions can be formulated for medical and/or veterinary use.

In some embodiments, the pharmaceutically acceptable carrier comprises a liposome. In some embodiments of the pharmaceutical composition, the compound is contained in a liposome or microsphere.

Methods

Also disclosed herein are methods of method of treating a subject with a disease comprising administering to the subject a compound disclosed herein. In some embodiments, the disease is an inflammatory disease. In some embodiments, the disease comprises chronic inflammation. Non-limiting examples of inflammatory diseases include arthritis (e.g., osteoarthritis, rheumatoid arthritis, collagen antibody-induced arthritis), asthma, chronic peptic ulcer, tuberculosis, periodontitis, ulcerative colitis, Crohn's disease, sinusitis, hepatitis, bronchitis, appendicitis, dermatitis, meningitis, ankylosing spondylitis, celiac disease, idiopathic pulmonary fibrosis, lupus, systemic lupus erythematosus, psoriasis, type 1 diabetes, Addison's disease, allergy, arthritis, prostatitis, diverticulitis, glomerulonephritis, hidradenitis suppurativa, inflammatory bowel disease, interstitial cystitis, mast cell activation syndrome, mastocytosis, otitis, pelvic inflammatory disease, reperfusion injury, rheumatic fever, rhinitis, sarcoidosis, transplant rejection, vasculitis, atherosclerosis, gout, pleurisy, eczema, gastritis, splenitis, laryngitis, thyroiditis, pharyngitis, multiple sclerosis, myopathies, seborrheic dermatitis, Wegener's granulomatosis, acne vulgaris, Alzheimer's disease, autoimmune diseases, hypersensitivities, Parkinson's disease, etc., and combinations thereof.

In some embodiments, the disease is Myelodysplastic Syndrome (MDS). MDSs are hematological (blood-related) medical conditions with ineffective production (or dysplasia) of the myeloid class of blood cells. In some cases, a subject with MDS has a chromosome 5q deletion (del(5q)). However, in other cases, the subject has non-del5q MDS. In some embodiments, the myeloid disorder is a myelodysplastic/myeloproliferative neoplasms (MDS/MPN). In some cases, the myeloid disorder is a myelodysplastic syndrome with myeloproliferative features. In some cases, the myeloid disorder is a therapy-related myeloid neoplasm.

In some embodiments, the Myelodysplastic Syndrome (MDS) is primary (where no apparent risk factors are found) or secondary (where the MDS develops after being exposed to, for example, chemotherapy or radiation therapy, or exposure to industrial chemicals such as benzene).

The first International Prognostic Scoring System (IPSS) was derived from a study published in 1997 and separates patients into four categories: low risk, intermediate-1 risk, intermediate-2 risk, and high risk (Greenberg P, Cox C, LeBeau M M, et al. International scoring system for evaluating prognosis in myelodysplastic syndromes. Blood 1997; 89:2079-2088). A revised IPSS was developed in 2012 and separates patients into five categories: very low risk, low risk, intermediate risk, high risk, and very high risk (Greenberg PL, Tuechler H, Schanz J, et al. Revised international prognostic scoring system for myelodysplastic syndromes. Blood 2012; 120:2454-2465).

In some aspects, methods of inhibiting inflammasome, the method comprising contacting inflammasome with a compound described herein are disclosed. In some embodiments, the methods treat a subject by reducing inflammation and/or pain. In some embodiments, the methods treat a subject by reducing inflammasome formation. In some embodiments, the methods treat a subject by reducing binding between two or more pyrin domains. In some embodiments, the methods treat a subject by reducing ASC speck formation. In some embodiments, the methods treat a subject by reducing caspase 1 activation.

The subject can be any mammalian subject, for example a human, dog, cow, horse, mouse, rabbit, etc. In some embodiments, the subject is a primate, particularly a human. The subject can be a male or female of any age, race, creed, ethnicity, socio-economic status, or other general classifiers.

The administering step can include at least one, at least two, at least three, at least four, at least five, at least six, at least seven, at least eight, at least nine, or at least ten dosages. The administering step can be performed before the subject exhibits disease symptoms (e.g., prophylactically), or during or after disease symptoms occur. The administering step can be performed prior to, concurrent with, or subsequent to administration of other agents to the subject. In some embodiments, the administering step is performed prior to, concurrent with, or subsequent to the administration of one or more additional diagnostic or therapeutic agents.

In some embodiments, a subsequent administration is provided at least one day after a prior administration, or at least two days, at least three days, at least four days, at least five days, or at least six days after a prior administration. In some embodiments, a subsequent administration is provided at least one week after a prior administration, or at least two weeks, at least three weeks, or at least four weeks after a prior administration. In some embodiments, a subsequent administration is provided at least one month, at least two months, at least three months, at least six months, or at least twelve months after a prior administration.

The amount of the disclosed compositions administered to a subject will vary from subject to subject, depending on the nature of the disclosed compositions and/or formulations, the species, gender, age, weight and general condition of the subject, the mode of administration, and the like. Effective dosages and schedules for administering the compositions may be determined empirically, and making such determinations is within the skill in the art. The dosage ranges for the administration of the disclosed compositions are those large enough to produce the desired effect (e.g., to reduce tumor size). The dosage should not be so large as to outweigh benefits by causing adverse side effects, such as unwanted cross-reactions, anaphylactic reactions, and the like, although some adverse side effects may be expected. The dosage can be adjusted by the individual clinician in the event of any counterindications. Generally, the disclosed compositions and/or formulations are administered to the subject at a dosage of active component(s) ranging from 0.1 µg/kg body weight to 100 g/kg body weight. In some embodiments, the disclosed compositions and/or formulations are administered to the subject at a dosage of active component(s) ranging from 1 µg/kg to 10 g/kg, from 10 µg/kg to 1 g/kg, from 10 µg/kg to 500 mg/kg, from 10 µg/kg to 100 mg/kg, from 10 µg/kg to 10 mg/kg, from 10 µg/kg to 1 mg/kg, from 10 µg/kg to 500 µg/kg, or from 10 µg/kg to 100 µg/kg body weight. Dosages above or below the range cited above may be administered to the individual subject if desired.

The disclosed compounds can be administered either sequentially or simultaneously in separate or combined pharmaceutical formulations. When one or more of the disclosed compounds is used in combination with a second therapeutic agent the dose of each compound can be either the same as or differ from that when the compound is used alone. Appropriate doses will be readily appreciated by those skilled in the art.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly [bis(p-carboxyphenoxy) propane:sebacic acid] in a 20:80 molar ratio (as used in GLIADEL); chondroitin; chitin; and chitosan.

In some embodiments, the methods are performed in a cell. In some embodiments, the cell is a myeloid cell. In some embodiments, the cell is a monocyte. In some embodiments, the cell is an inflammatory mediator.

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Kits

Kits for practicing the methods of the invention are further provided. By "kit" is intended any manufacture (e.g., a package or a container) comprising at least one reagent, e.g., anyone of the compounds described in Table 1. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

Methods of Synthesis

Methods of synthesizing the compounds described herein are disclosed. The method of synthesizing the compounds can include reacting glyoxalic acid with methyl thryptophanate to form a first intermediate; condensing the first intermediate with an amine to form a second intermediate; and oxidizing the second intermediate to form a first product.

The methods can further include hydrolyzing the first product in the presence of a base followed by acidifying to give a third intermediate; and reacting the third intermediate with an amine to form a second product.

EXAMPLES

To further illustrate the principles of the present disclosure, the following examples are put forth so as to provide those of ordinary skill in the art with a complete disclosure and description of how the compositions, articles, and methods claimed herein are made and evaluated. They are intended to be purely exemplary of the invention and are not intended to limit the scope of what the inventors regard as their disclosure. These examples are not intended to exclude equivalents and variations of the present invention which are apparent to one skilled in the art. Unless indicated otherwise, temperature is ° C. or is at ambient temperature, and pressure is at or near atmospheric. There are numerous variations and combinations of process conditions that can be used to optimize product quality and performance. Only reasonable and routine experimentation will be required to optimize such process conditions.

Example 1. Small-Molecule NLRP3 Inflammasome Inhibitors $ASC^{PYD}/ASC^{PYD}$ and $NLRP3^{PYD}/ASC^{PYD}$ binary PPIs are weak ($K_D$=65 and 22 UM, respectively (Oroz et al., 2016)), while the NLRP3 inflammasome structure is large. These characteristics make it difficult to screen small-molecule inhibitors for inflammasome in biochemical settings. Disclosed in this example is establishment of a FP competitive inhibition assay to screen small-molecule libraries for inflammasome inhibition.

The compounds in Scheme 1 have been shown to disrupt $NLRP3^{PYD}$/fSAH-POP1-12 PPI.

Scheme 1: Structures and the protein-protein (PPI) inhibition activities of small molecules.

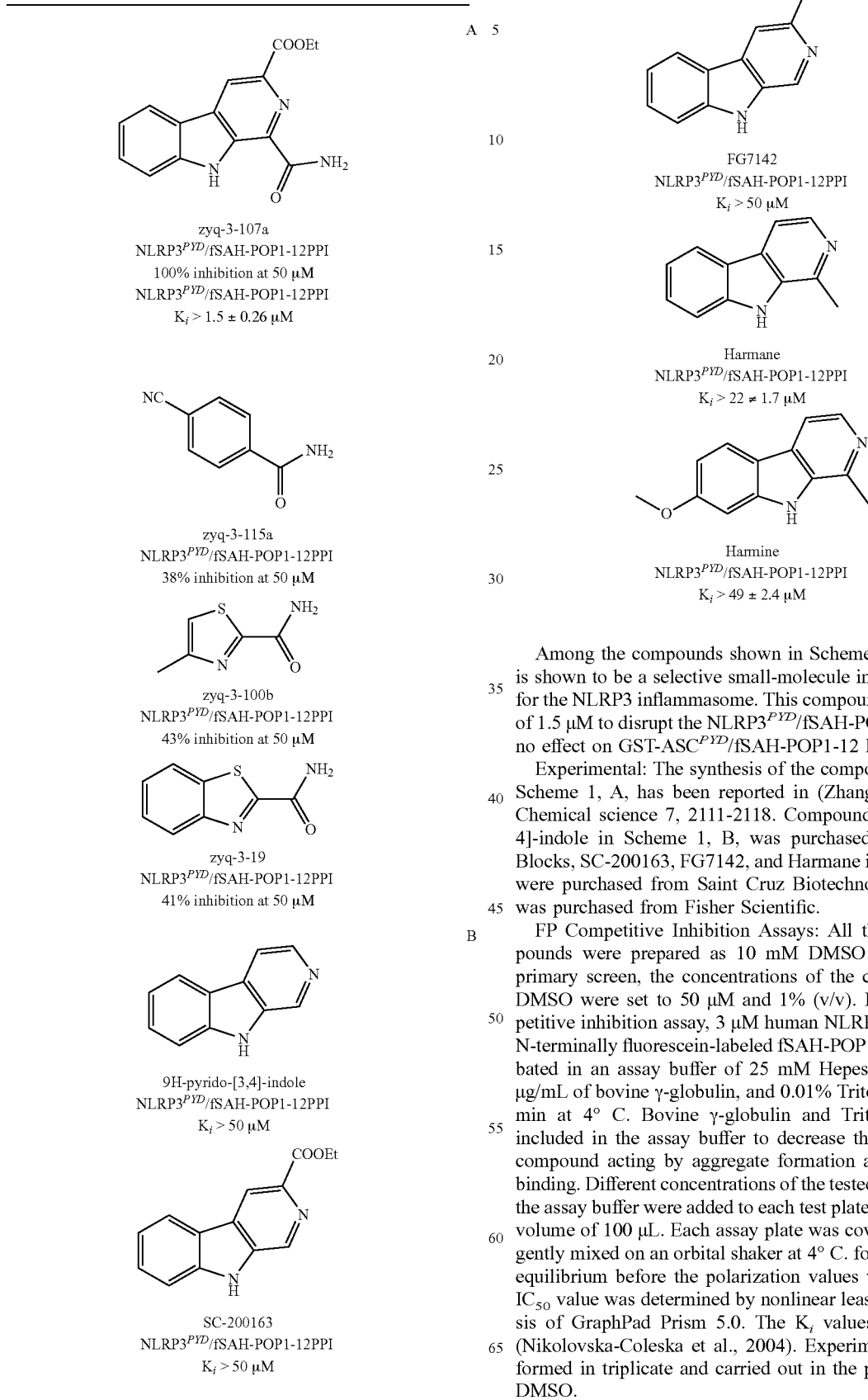

Among the compounds shown in Scheme 1, zyq-3-107a is shown to be a selective small-molecule inhibitor specific for the NLRP3 inflammasome. This compound exhibits a $K_i$ of 1.5 µM to disrupt the NLRP3$^{PYD}$/fSAH-POP1-12 PPI but no effect on GST-ASC$^{PYD}$/fSAH-POP1-12 PPI.

Experimental: The synthesis of the compounds shown in Scheme 1, A, has been reported in (Zhang et al., 2016), Chemical science 7, 2111-2118. Compound 9H-pyrido-[3,4]-indole in Scheme 1, B, was purchased from Combi-Blocks, SC-200163, FG7142, and Harmane in Scheme 1, B, were purchased from Saint Cruz Biotechnology. Harmine was purchased from Fisher Scientific.

FP Competitive Inhibition Assays: All the tested compounds were prepared as 10 mM DMSO stocks. In the primary screen, the concentrations of the compounds and DMSO were set to 50 µM and 1% (v/v). In the FP competitive inhibition assay, 3 µM human NLRP3 and 5 nM of N-terminally fluorescein-labeled fSAH-POP1-12 were incubated in an assay buffer of 25 mM Hepes (pH 7.4), 100 µg/mL of bovine γ-globulin, and 0.01% Triton-X100 for 15 min at 4° C. Bovine γ-globulin and Triton-X100 were included in the assay buffer to decrease the likelihood of compound acting by aggregate formation and nonspecific binding. Different concentrations of the tested compounds in the assay buffer were added to each test plate to make a final volume of 100 µL. Each assay plate was covered black and gently mixed on an orbital shaker at 4° C. for 1.5 h to reach equilibrium before the polarization values were read. The $IC_{50}$ value was determined by nonlinear least-square analysis of GraphPad Prism 5.0. The $K_i$ values were derived (Nikolovska-Coleska et al., 2004). Experiments were performed in triplicate and carried out in the presence of 1% DMSO.

Example 2: Chemical Synthesis of Small-Molecule NLRP3 Inflammasome Inhibitors

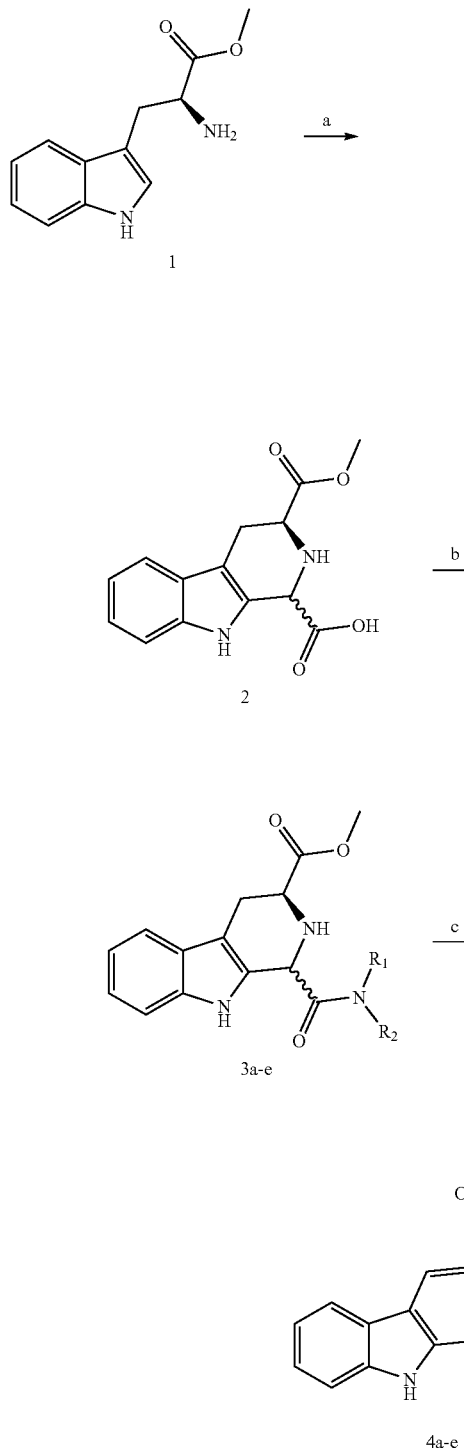

Scheme 1. Synthesis of carboline derivatives 4a-e.

Reagents and conditions: (a) HCO—COOH, EtOAc, rt, 16 h; (b) HATU, DIEPA, amines, CH$_2$Cl$_2$, rt, 24 h. (c) MnO$_2$, 100° C., 16 h.

In this example, the intermediate 3-(methoxycarbonyl)-9H-pyrido[3,4-b]indole-1-carboxylic acid was synthesized. A search through the literature revealed that there was no report of the synthesis of the acid. Therefore, Scheme 1 was adopted in the present study. Firstly, a modification of the Pictet-Spengler reaction between L-tryptophan methyl ester and glyoxylic acid gave 2 (Scheme 1). Condensation of 2 with different amines in the presence of HATU and DIEPA in CH$_2$Cl$_2$ provided amide 3 in good yield. Finally, oxidation of 3 with MnO$_2$ at 100° C. over 16 h afforded 4a-e.

The synthesis of target compounds 6a-k was started from the intermediate 4a. LiOH was used as a base and methanol as the solvent, and reacted at room temperature, 40° C., 60° C., and 80° C., respectively. It was found that the first three reaction were slow, and after 8 h, the raw material 4a did not disappear. While the reaction was rapid under the conditions of 80° C., and the raw material disappeared after 2 h, however, by-product was formed. Therefore, 4a was hydrolyzed in the presence of NaOH, and then acidified to obtain intermediate 5, the yield was good and there was no by-product formed. Subsequently, reaction of 5 with different amines in the presence of HATU/DIEPA afforded the target compounds 6a-k which were purified by column chromatography to give the pure products. The yields were from 50% to 83%.

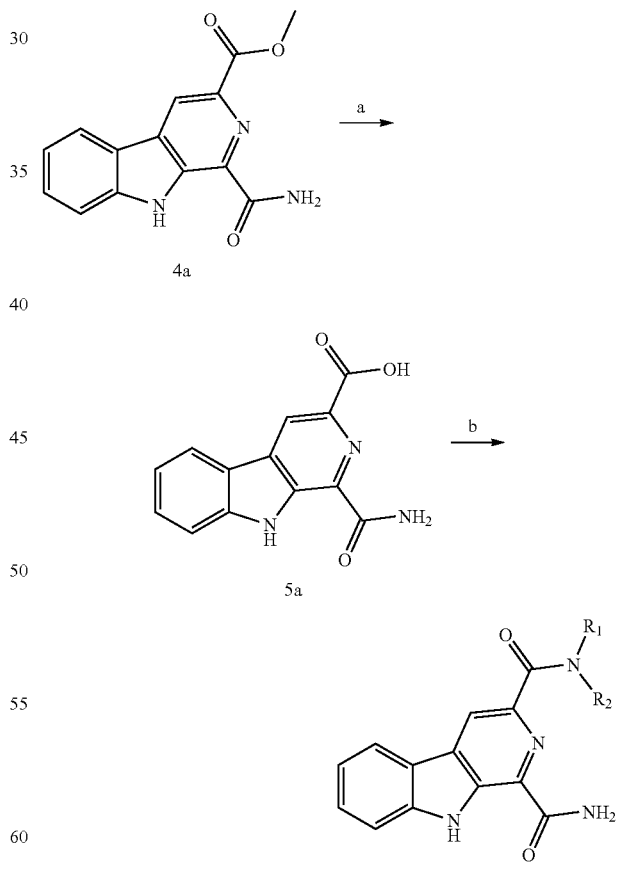

Scheme 2. Synthesis of carboline derivatives 6a-x.

Reagents and conditions: (a) NaOH, THF/MeOH/H$_2$O, rt, overnight; (b) HATU, DIPEA, amines, CH$_2$Cl$_2$, rt, overnight.

Structures
TABLE 1
Inhibition of protein-protein interaction.
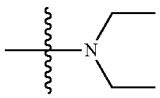
| Compounds | NR₁R₂ | NR₃R₄ |
|---|---|---|
| 4a | NH₂ | — |
| 4b | 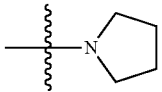 [SMILES: *N1CCCC1] | — |
| 4c | 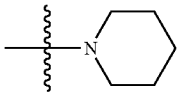 [SMILES: *N1CCCCC1] | — |
| 4d | 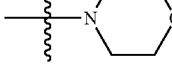 | — |
| 4e | 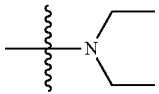 | — |
| 6a | NH₂ | 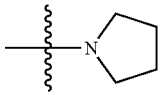 [SMILES: *N1CCCC1] |
| 6b | NH₂ | 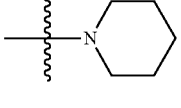 |
| 6c | NH₂ | 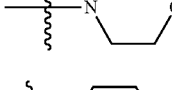 |
| 6d | NH₂ | 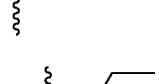 |
| 6e | NH₂ | 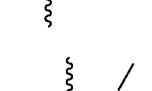 |
| 6f | NH₂ | 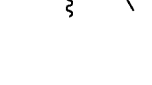 |
| 6g | NH₂ |  |
TABLE 1-continued
Inhibition of protein-protein interaction.
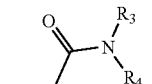
| Compounds | NR₁R₂ | NR₃R₄ |
|---|---|---|
| 6h | NH₂ | 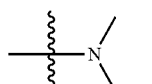 |
| 6i | NH₂ | 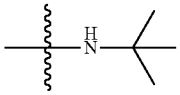 [SMILES: *NC(C)(C)C] |
| 6j | NH₂ | 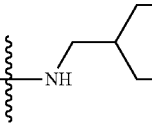 |
| 6k | NH₂ | 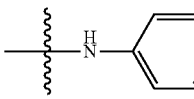 |
| 6l | 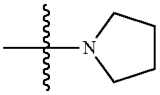 [SMILES: *N1CCCC1] | 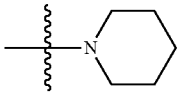 |
| 6m | 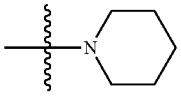 | 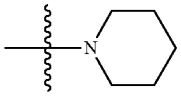 |
| 6n | NH₂ | 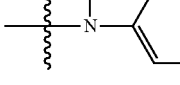 |
| 6o | NH₂ | 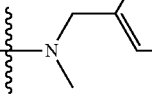 |
| 6p | NH₂ | 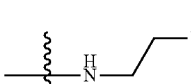 |
| 6q | NH₂ |  |

TABLE 1-continued

Inhibition of protein-protein interaction.

[Structures of 4a-e and 6a-x: methyl pyrido[3,4-b]indole-3-carboxylate with 1-carboxamide NR₁R₂ (4a-e), and the diamide analog with NR₃R₄ at position 3 and NR₁R₂ at position 1 (6a-x)]

| Compounds | NR₁R₂ | NR₃R₄ |
|---|---|---|
| 6r | NH₂ | —N(piperazinyl)NBoc |
| 6s | NH₂ | —N(piperazinyl)NH |
| 6t | NH₂ | —OH (attached via CH) |
| 6u | NH₂ | cis-octahydropyrrolo[3,4-b]pyrrole-NH |
| 6v | NH₂ | —NH-CH₂CH₂-OH |
| 6w | NH₂ | (S)-3-hydroxypyrrolidin-1-yl |
| 6x | NH₂ | (R)-3-hydroxypyrrolidin-1-yl |

Experimental Section

Chemistry Synthesis. General Methods, Reagents and Materials. All reagents were purchased from commercial sources and used without further purification. Reactions were followed by TLC on E. Merck precoated silica gel 60 F254 plates, and the spots were visualized using a UV lamp ($\lambda$=254 nm). Chromatographic separations were performed with SilicaFlash F60 (230-400 mesh) by flash chromatography. $^{1}$H NMR and $^{13}$C NMR spectra were recorded on the Bruker AVANCEIIIHD 500 (500 MHz) spectrometers (125 MHz for $^{13}$C NMR spectra) in $d_6$-DMSO, $d_4$-methanol, and CDCl$_3$. Chemical shifts are reported in parts per millions (ppm) relative to tetramethylsilane (TMS), and spin multiplicities are given as s (singlet), brs (broad singlet), d (doublet), t (triplet), q (quartet), or m (multiplet). Low-resolution mass spectra were determined on the Agilent 6120 single quadrupole MS with 1220 infinity LC system (HPLC-MS) with an ESI source. High-resolution mass spectra were determined on the Agilent G6230BA TOF LCMS Mass Spectrometer with a TOF mass detector.

Synthesis Procedure of the intermediate. To a stirred solution of methyl thryptophanate (8.0 g, 36.7 mmol) in 50 mL of EtOAc were added 3.33 g (36.7 mmol) of glyoxalic acid, and the mixture was maintained at room temperature over 16 h. The precipitate formed was filtered and washed with EtOAc to give 8.0 g (84%) of 2.

General Procedures for the Preparation of the intermediate 3a-e: The intermediate 2 (0.54 g, 2.0 mmol), amine (3.0 mmol), HATU (1.14 g, 3 mmol) and DIEPA (0.42 g, 4 mmol) were stirred in CH$_2$Cl$_2$ (30 mL) at room temperature, and the reaction mixture was stirred at room temperature for 24 h. The solvent was concentrated under reduced pressure, and EtOAc (30 mL) was added, the mixture was washed with water (30 mL×2) and brine (30 mL×2). The organic layer was dried over Na$_2$SO$_4$ and concentrated under reduced pressure. The residue was purified by column chromatography using CH$_2$Cl$_2$:MeOH (40:1, v/v) to provide the intermediates 3a-e.

General Procedures for the Preparation of the intermediate 4a-e: A solution of the intermediates 3 (2 mmol) and MnO$_2$ (0.52 g, 6 mmol) in toluene (20 mL) was stirred at 100° C. for 16 h. When the reaction had completed, ice water (40 mL) was added to the mixture before extraction using CH$_2$Cl$_2$. The combined organic layers were dried over NaSO$_4$ and concentrated under reduced pressure. The crude product was purified on silica gel and eluted using CH$_2$Cl$_2$: MeOH (50:1, v/v) to obtain the intermediates 4a-e.

Methyl 1-carbamoyl-9H-pyrido[3,4-b]indole-3-carboxylate (4a). Yield: 45%; white solid; $^{1}$H NMR (500 MHz, Chloroform-d) δ 10.47 (s, 1H), 8.91 (s, 1H), 8.26 (s, 1H), 8.14 (d, J=8.0 Hz, 1H), 7.59-7.54 (m, 2H), 7.32 (t, J=7.2 Hz, 1H), 5.68 (s, 1H), 3.99 (s, 3H). $^{13}$C NMR (126 MHz, CDCl$_3$) δ 166.02, 141.37, 141.23, 137.01, 135.97, 129.78, 122.04, 121.33, 120.97, 120.44, 112.35, 112.30, 52.69. ESI-MS m/z: 270.1 [M+H]$^{+}$; Purity: 99.5% by HPLC.

Methyl 1-(diethylcarbamoyl)-9H-pyrido[3,4-b]indole-3-carboxylate (4b). Yield: 56%; white solid; $^{1}$H NMR (500 MHz, CDCl$_3$) δ 10.36 (s, 1H), 8.84 (d, J=0.7 Hz, 1H), 8.10 (d, J=7.8 Hz, 1H), 7.54-7.49 (m, 1H), 7.46 (d, J=8.2 Hz, 1H), 7.30-7.24 (m, 1H), 4.00-3.92 (m, 5H), 3.59 (q, J=7.0 Hz, 2H), 1.39 (t, J=7.0 Hz, 3H), 1.28 (t, J=7.0 Hz, 3H). $^{13}$C NMR (126 MHz, CDCl$_3$) δ 166.51, 166.40, 140.88, 137.92, 135.22, 134.80, 130.88, 129.29, 121.78, 121.40, 120.98, 119.12, 112.21, 52.45, 44.28, 42.36, 14.58, 12.81. ESI-MS m/z: 326.2 [M+H]$^{+}$; Purity: 99.3% by HPLC.

Methyl 1-(pyrrolidine-1-carbonyl)-9H-pyrido[3,4-b]indole-3-carboxylate (4c). Yield: 69%; pale yellow solid; $^{1}$H NMR (500 MHz, Chloroform-d) δ 10.55 (s, 1H), 8.84 (s, 1H), 8.11 (d, J=8.0 Hz, 1H), 7.54-7.50 (m, 1H), 7.48 (d, J=8.0 Hz, 1H), 7.30-7.24 (m, 1H), 4.27 (t, J=6.8 Hz, 2H), 3.97 (s, 3H), 3.72 (t, J=6.8 Hz, 2H), 2.00-1.94 (m, 2H), 1.89 (p, J=7.7, 7.1 Hz, 2H). $^{13}$C NMR (125 MHz, CDCl$_3$) δ 166.37, 165.39, 140.89, 137.89, 135.34, 134.67, 130.79, 129.30, 121.80, 121.29, 121.00, 119.23, 112.24, 52.57, 49.93, 47.77, 27.12, 23.66. ESI-MS m/z: 324.2 [M+H]$^{+}$; Purity: 96.4% by HPLC.

Methyl 1-(piperidine-1-carbonyl)-9H-pyrido[3,4-b]indole-3-carboxylate (4d). Yield: 50%; white solid; $^{1}$H NMR (500 MHz, Chloroform-d) δ 10.28 (s, 1H), 8.82 (s, 1H), 8.08 (d, J=7.9 Hz, 1H), 7.51-7.47 (m, 1H), 7.43 (d, J=8.2 Hz, 1H), 7.25 (t, J=7.5 Hz, 1H), 4.14 (d, J=5.4 Hz, 2H), 3.97 (s, 3H), 3.77 (d, J=4.8 Hz, 2H), 1.67 (d, J=8.7 Hz, 6H). $^{13}$C NMR (125 MHz, CDCl$_3$) δ 166.29, 165.73, 141.01, 137.83, 135.20, 134.89, 130.98, 129.35, 121.76, 121.37, 121.01, 119.06, 112.25, 52.62, 48.70, 44.39, 26.85, 25.93, 24.72. ESI-MS m/z: 338.2 [M+H]$^+$; Purity: 100% by HPLC.

Methyl 1-(morpholine-4-carbonyl)-9H-pyrido[3,4-b]indole-3-carboxylate (4e). Yield: 65%; white solid; $^1$H NMR (500 MHz, Chloroform-d) δ 10.39 (s, 1H), 8.90 (s, 1H), 8.15 (d, J=8.2 Hz, 1H), 7.60-7.55 (m, 1H), 7.52 (d, J=8.2 Hz, 1H), 7.33 (t, J=7.5 Hz, 1H), 4.57-4.50 (m, 2H), 4.03 (s, 3H), 3.94-3.90 (m, 2H), 3.89-3.86 (m, 2H), 3.85-3.82 (m, 2H). $^{13}$C NMR (126 MHz, CDCl$_3$) δ 166.05, 165.57, 140.98, 138.06, 135.08, 133.84, 131.29, 129.54, 121.83, 121.27, 121.18, 119.38, 112.25, 67.39, 67.02, 52.67, 48.32, 43.61. ESI-MS m/z: 340.2 [M+H]$^+$; Purity: 98.6% by HPLC.

Preparation of the intermediate 5a. A solution of the intermediates 4a (1.08 g, 4 mmol) and NaOH (0.80 g, 20 mmol) in a mixture of THF/MeOH/H$_2$O (v:v:v=4:2:1, 35 mL) was stirred at room temperature for 12 h. When the reaction had completed, diluted HCl solution was added to adjust the pH=2-3, filtered under reduced pressure, the filter cake was washed three times with water, dried in vacuum to obtain compound 5a as white solid (1.00 g, yield 98%).

General Procedures for the Preparation of 6a-x. The intermediate 5a (0.25 g, 1.0 mmol), amine (1.2 mmol), HATU (0.38 g, 1.0 mmol) and DIEPA (0.13 g, 1.0 mmol) were stirred in CH$_2$Cl$_2$ (20 mL), and the reaction mixture was stirred at room temperature for 24 h. The solvent was concentrated under reduced pressure, and EtOAc (30 mL) was added, the mixture was washed with water (30 mL×2) and brine (30 mL×2). The organic layer was dried over Na$_2$SO$_4$ and concentrated under reduced pressure. The residue was purified by column chromatography using CH$_2$Cl$_2$:MeOH (40:1, v/v) to provide 6a-x.

N$^3$,N$^3$-Diethyl-9H-pyrido[3,4-b]indole-1,3-dicarboxamide (6a). $^1$H NMR (500 MHz, Chloroform-d) δ 10.39 (s, 1H), 8.52 (s, 1H), 8.14 (d, J=8.3 Hz, 1H), 7.82 (s, 1H), 7.63-7.57 (m, 2H), 7.35-7.30 (m, 1H), 6.01 (s, 1H), 3.64 (q, J=7.0 Hz, 2H), 3.48 (q, J=6.5 Hz, 2H), 1.33 (t, J=7.0 Hz, 3H), 1.26 (t, J=7.0 Hz, 3H). $^{13}$C NMR (125 MHz, CDCl$_3$) δ 168.79, 168.69, 143.06, 141.46, 135.75, 132.18, 129.63, 129.09, 122.12, 120.86, 120.83, 118.72, 112.09, 43.41, 40.51, 14.68, 12.92. ESI-MS m/z: 311.2 [M+H]$^+$; Purity: 100% by HPLC.

3-(Pyrrolidine-1-carbonyl)-9H-pyrido[3,4-b]indole-1-carboxamide (6b). $^1$H NMR (500 MHz, Chloroform-d) δ 8.70 (s, 1H), 8.15 (d, J=7.8 Hz, 1H), 7.61-7.55 (m, 2H), 7.58-7.29 (m, 1H), 3.83 (t, J=6.5 Hz, 2H), 3.72 (d, J=6.5 Hz, 2H), 1.99-1.91 (m, 4H). $^{13}$C NMR (125 MHz, CDCl$_3$) δ 166.92, 141.93, 141.39, 135.78, 132.04, 129.64, 129.05, 122.07, 120.95, 120.83, 119.26, 112.11, 53.41, 47.24, 26.77, 24.02. ESI-MS m/z: 309.1 [M+H]$^+$; Purity: 100% by HPLC.

3-(Piperidine-1-carbonyl)-9H-pyrido[3,4-b]indole-1-carboxamide (6c). $^1$H NMR (500 MHz, Chloroform-d) δ 10.45 (s, 1H), 8.50 (s, 1H), 8.13 (d, J=8.5 Hz, 1H), 7.87 (s, 1H), 7.63-7.55 (m, 2H), 7.33-7.30 (m, 1H), 6.19 (s, 1H), 3.68 (s, 4H), 1.72 (s, 6H). $^{13}$C NMR (125 MHz, CDCl$_3$) δ 168.22, 167.55, 142.23, 141.55, 135.71, 132.41, 129.86, 128.92, 122.19, 121.01, 120.75, 118.82, 112.13, 26.22, 24.69. ESI-MS m/z: 323.2 [M+H]$^+$; Purity: 100% by HPLC.

3-(Morpholine-4-carbonyl)-9H-pyrido[3,4-b]indole-1-carboxamide (6d). $^1$H NMR (500 MHz, DMSO-d$_6$) δ 11.86 (s, 1H), 8.65 (s, 1H), 8.35 (d, J=8.0 Hz, 1H), 8.06 (s, 1H), 7.86 (s, 1H), 7.84 (d, J=8.5 Hz, 1H), 7.60 (t, J=7.5 Hz, 1H), 7.30 (t, J=7.5 Hz, 1H), 3.73 (s, 4H), 3.62 (s, 4H). $^{13}$C NMR (125 MHz, DMSO) δ 167.83, 167.56, 142.44, 141.35, 134.94, 131.77, 130.86, 129.58, 122.51, 120.66, 120.56, 119.05, 113.68, 66.80, 66.59, 48.05, 42.84. ESI-MS m/z: 325.2 [M+H]$^+$; Purity: 99.9% by HPLC.

N$^3$-Butyl-9H-pyrido[3,4-b]indole-1,3-dicarboxamide (6e). $^1$H NMR (500 MHz, DMSO-d$_6$) δ 11.93 (s, 1H), 9.31 (t, J=6.0 Hz, 1H), 9.07 (s, 1H), 8.41 (d, J=8.0 Hz, 1H), 7.89 (s, 1H), 7.85 (d, J=8.2 Hz, 1H), 7.60 (t, J=7.7 Hz, 1H), 7.31 (t, J=7.5 Hz, 1H), 3.39 (q, J=7.0 Hz, 2H), 1.62-1.56 (m, 2H), 1.41-1.34 (m, 2H), 0.94 (t, J=7.5 Hz, 3H). $^{13}$C NMR (126 MHz, DMSO) δ 167.97, 164.47, 142.46, 138.81, 135.94, 131.87, 131.19, 129.48, 122.55, 120.84, 120.76, 116.91, 113.71, 39.00, 32.24, 20.25, 14.26. ESI-MS m/z: 311.2 [M+H]$^+$; Purity: 95.6% by HPLC.

N$^3$-Ethyl-9H-pyrido[3,4-b]indole-1,3-dicarboxamide (6f). $^1$H NMR (500 MHz, DMSO-d$_6$) δ 11.95 (s, 1H), 9.36 (t, J=6.0 Hz, 1H), 9.13-9.04 (m, 1H), 9.00 (s, 1H), 8.41 (d, J=8.0 Hz, 1H), 7.91 (t, J=3.0 Hz, 1H), 7.88-7.82 (m, 1H), 7.59 (t, J=7.7 Hz, 1H), 7.30 (t, J=7.5 Hz, 1H), 3.45-3.39 (m, 2H), 1.20 (t, J=7.2 Hz, 3H). $^{13}$C NMR (126 MHz, DMSO) δ 167.96, 164.34, 142.46, 138.80, 135.93, 131.87, 131.19, 129.49, 122.58, 120.83, 120.76, 116.90, 113.72, 34.07, 15.74. ESI-MS m/z: 283.1 [M+H]$^+$; Purity: 100% by HPLC.

N$^3$,N$^3$-Dimethyl-9H-pyrido[3,4-b]indole-1,3-dicarboxamide (6g). $^1$H NMR (500 MHz, DMSO-d$_6$) δ 11.84 (s, 1H), 8.62 (s, 1H), 8.35 (d, J=7.8 Hz, 1H), 8.12 (s, 1H), 7.83 (d, J=8.2 Hz, 2H), 7.59 (t, J=8.0 Hz, 1H), 7.29 (t, J=7.5 Hz, 1H), 3.11 (s, 3H), 3.08 (s, 3H). $^{13}$C NMR (125 MHz, DMSO) δ 168.27, 167.45, 141.96, 141.71, 134.39, 131.20, 130.28, 129.06, 122.03, 120.12, 120.11, 118.17, 113.18, 38.96, 35.46. ESI-MS m/z: 283.2 [M+H]$^+$; Purity: 100% by HPLC.

N$^3$-Ethyl-N$^3$-methyl-9H-pyrido[3,4-b]indole-1,3-dicarboxamide (6h). $^1$H NMR (500 MHz, DMSO-d$_6$) δ 11.83 (s, 1H), 8.60 (d, J=26.0 Hz, 1H), 8.35 (d, J=7.8 Hz, 1H), 8.06 (d, J=54.0 Hz, 1H), 7.91-7.79 (m, 2H), 7.59 (t, J=7.7 Hz, 1H), 7.29 (t, J=7.8 Hz, 1H), 3.54 (q, J=7.0 Hz, 1H), 3.38 (q, J=7.0 Hz, 1H), 3.06 (d, J=19.5 Hz, 3H), 1.18 (dt, J=26.4, 7.1 Hz, 3H). $^{13}$C NMR (125 MHz, DMSO) δ 169.00, 167.92, 142.45, 134.82, 131.73, 130.92, 130.67, 129.56, 122.53, 120.57, 118.68, 118.14, 113.64, 45.70, 42.75, 36.79, 32.85, 14.08, 12.49. ESI-MS m/z: 297.2 [M+H]$^+$; Purity: 95.0% by HPLC.

N$^3$-(tert-Butyl)-9H-pyrido[3,4-b]indole-1,3-dicarboxamide (6i). $^1$H NMR (500 MHz, DMSO-d$_6$) δ 11.92 (s, 1H), 9.04 (s, 1H), 9.01 (s, 1H), 8.44 (s, 1H), 8.38 (d, J=8.0 Hz, 1H), 7.87 (s, 1H), 7.85 (d, J=8.2 Hz, 1H), 7.60 (t, J=8.2 Hz, 1H), 7.30 (t, J=7.5 Hz, 1H), 1.49 (s, 9H). $^{13}$C NMR (125 MHz, DMSO) δ 167.59, 163.62, 142.06, 139.19, 135.62, 131.38, 130.88, 129.08, 122.08, 120.39, 120.33, 116.46, 113.30, 50.67, 28.85. ESI-MS m/z: 311.2 [M+H]$^+$; Purity: 95.8% by HPLC.

N$^3$-(Cyclohexylmethyl)-9H-pyrido[3,4-b]indole-1,3-dicarboxamide (6j). $^1$H NMR (500 MHz, DMSO-d$_6$) δ 11.93 (s, 1H), 9.30 (t, J=6.3 Hz, 1H), 9.08 (s, 1H), 8.98 (s, 1H), 8.40 (d, J=8.0 Hz, 1H), 7.89 (s, 1H), 7.84 (d, J=8.3 Hz, 1H), 7.59 (t, J=7.7 Hz, 1H), 7.30 (t, J=7.5 Hz, 1H), 3.22 (t, J=6.5 Hz, 2H), 1.75-1.68 (m, 4H), 1.64-1.56 (m, 2H), 1.24-1.14 (m, 3H), 1.01-0.94 (m, 2H). $^{13}$C NMR (125 MHz, DMSO) δ 167.97, 164.58, 142.46, 138.79, 135.94, 131.86, 131.18, 129.47, 122.56, 120.83, 120.75, 116.98, 113.71, 45.57, 38.48, 31.14, 26.59, 25.95. ESI-MS m/z: 351.3 [M+H]$^+$; Purity: 95.2% by HPLC.

N$^3$-Phenyl-9H-pyrido[3,4-b]indole-1,3-dicarboxamide (6k). $^1$H NMR (500 MHz, DMSO-d$_6$) δ 11.77 (s, 1H), 8.78 (s, 1H), 8.34 (d, J=8.0 Hz, 1H), 7.78 (d, J=8.2 Hz, 1H), 7.60 (s, 1H), 7.57 (t, J=7.7 Hz, 1H), 7.29 (t, J=7.5 Hz, 1H), 7.26-7.21 (m, 4H), 7.14 (t, J=6.7 Hz, 1H), 6.78 (s, 1H), 3.48 (s, 3H). $^{13}$C NMR (125 MHz, DMSO) δ 167.35, 166.89, 145.80, 141.91, 140.33, 133.97, 131.00, 129.52, 129.08, 128.91, 126.46, 126.05, 121.99, 120.31, 120.11, 119.28, 113.22, 38.39. ESI-MS m/z: 331.2 [M+H]$^+$; Purity: 98.4% by HPLC.

Piperidin-1-yl(1-(pyrrolidine-1-carbonyl)-9H-pyrido[3,4-b]indol-3-yl)methanone (6m). $^1$H NMR (500 MHz, Chloroform-d) δ 9.82 (s, 1H), 8.73 (s, 1H), 8.16 (d, J=8.2 Hz, 1H), 7.59-7.56 (m, 1H), 7.51 (d, J=8.2 Hz, 1H), 7.32 (t, J=7.5 Hz, 1H), 4.11 (s, 2H), 3.87 (t, J=6.5 Hz, 2H), 3.83 (s, 2H), 3.76 (t, J=6.5 Hz, 2H), 1.98-1.93 (m, 4H), 1.75 (s, 4H), 1.65 (s, 4H). $^{13}$C NMR (125 MHz, CDCl$_3$) δ 166.93, 166.27, 141.77, 140.89, 136.90, 132.87, 131.30, 129.19, 122.01, 121.54, 120.70, 118.17, 111.89, 49.45, 48.32, 47.25, 44.13, 27.01, 26.85, 25.93, 24.70, 24.08. ESI-MS m/z: 377.3 [M+H]$^+$; Purity: 99.8% by HPLC.

(9H-Pyrido[3,4-b]indole-1,3-diyl)bis(piperidin-1-yl-methanone) (6m). $^1$H NMR (500 MHz, Chloroform-d) δ 9.88 (s, 1H), 8.43 (s, 1H), 8.13 (d, J=7.8 Hz, 1H), 7.58 (t, J=7.5 Hz, 1H), 7.51 (d, J=8.2 Hz, 1H), 7.31 (t, J=7.5 Hz, 1H), 4.15 (t, J=5.5 Hz, 2H), 3.82 (d, J=5.2 Hz, 2H), 3.79 (d, J=6.0 Hz, 2H), 3.56 (t, J=5.5 Hz, 2H), 1.74 (s, 4H), 1.71 (s, 4H), 1.67-1.56 (m, 4H). $^{13}$C NMR (125 MHz, CDCl$_3$) δ 168.39, 166.03, 141.82, 140.86, 136.71, 133.12, 131.44, 129.23, 121.93, 121.33, 120.62, 117.55, 111.90, 48.57, 48.41, 44.29, 43.73, 26.95, 26.67, 26.01, 25.80, 24.73, 24.70. ESI-MS m/z: 391.3 [M+H]$^+$; Purity: 99.7% by HPLC.

N$^3$-Methyl-N$^3$-phenyl-9H-pyrido[3,4-b]indole-1,3-dicarboxamide (6n). $^1$H NMR (500 MHz, DMSO-d$_6$) δ 11.77 (s, 1H), 8.78 (s, 1H), 8.34 (d, J=8.0 Hz, 1H), 7.78 (d, J=8.2 Hz, 1H), 7.60 (s, 1H), 7.57 (t, J=7.7 Hz, 1H), 7.29 (t, J=7.5 Hz, 1H), 7.26-7.21 (m, 4H), 7.14 (t, J=6.7 Hz, 1H), 6.78 (s, 1H), 3.48 (s, 3H). $^{13}$C NMR (125 MHz, DMSO) δ 167.35, 166.89, 145.80, 141.91, 140.33, 133.97, 131.00, 129.52, 129.08, 128.91, 126.46, 126.05, 121.99, 120.31, 120.11, 119.28, 113.22, 38.39. ESI-MS m/z: 391.3 [M+H]$^+$; Purity: 99.7% by HPLC.

N$^3$-Benzyl-N$^3$-methyl-9H-pyrido[3,4-b]indole-1,3-dicarboxamide (6o). $^1$H NMR (500 MHz, DMSO-d$_6$) δ 11.85 (d, J=17.0 Hz, 1H), 8.74 (d, J=7.8 Hz, 1H), 8.38 (m, 1H), 7.99 (m, 1H), 7.83 (m, 1H), 7.63-7.56 (m, 1H), 7.50-7.35 (m, 3H), 7.35-7.23 (m, 4H), 4.77 (d, J=4.0 Hz, 2H), 3.05 (d, J=24.0 Hz, 3H). $^{13}$C NMR (125 MHz, DMSO) δ 169.17, 168.93, 167.90, 167.65, 142.45, 141.99, 141.66, 138.30, 137.95, 135.03, 134.94, 131.86, 131.74, 130.78, 130.42, 129.61, 129.55, 129.09, 129.03, 128.19, 127.64, 127.60, 127.14, 122.60, 122.56, 120.68, 120.65, 120.61, 120.55, 119.24, 118.99, 113.67, 54.62, 51.17, 37.38, 34.26. ESI-MS m/z: 359.2 [M+H]$^+$; Purity: 97.9% by HPLC.

N$^3$-(2-(Dimethylamino)ethyl)-9H-pyrido[3,4-b]indole-1,3-dicarboxamide (6p). $^1$H NMR (500 MHz, DMSO-d$_6$) δ 12.02 (s, 1H), 9.50 (s, 1H), 9.31 (s, 1H), 9.03 (s, 1H), 8.96 (s, 1H), 8.44 (d, J=7.8 Hz, 1H), 8.01 (s, 1H), 7.86 (d, J=8.2 Hz, 1H), 7.62 (t, J=7.5 Hz, 1H), 7.32 (t, J=7.5 Hz, 1H), 3.73 (q, J=6.5 Hz, 2H), 3.34 (t, J=5.5 Hz, 2H), 2.90 (s, 6H). $^{13}$C NMR (125 MHz, DMSO) δ 167.32, 165.22, 142.07, 137.47, 135.57, 131.46, 130.71, 129.20, 122.17, 120.45, 120.33, 116.71, 113.34, 56.42, 42.66, 34.41. ESI-MS m/z: 326.2 [M+H]$^+$; Purity: 97.4% by HPLC.

N$^3$-(3-(Pyrrolidin-1-yl)propyl)-9H-pyrido[3,4-b]indole-1,3-dicarboxamide (6q). $^1$H NMR (500 MHz, DMSO-d$_6$) δ 11.98 (s, 1H), 9.48 (t, J=6.2 Hz, 1H), 9.36 (s, 1H), 9.01 (s, 2H), 8.42 (d, J=8.0 Hz, 1H), 7.95 (s, 1H), 7.85 (d, J=8.2 Hz, 1H), 7.65-7.56 (m, 1H), 7.32 (t, J=7.5 Hz, 1H), 3.58 (s, 2H), 3.47 (q, J=6.5 Hz, 2H), 3.25-3.21 (m, 2H), 3.05-2.98 (m, 2H), 2.09-1.92 (m, 4H), 1.92-1.81 (m, 2H). $^{13}$C NMR (125 MHz, DMSO) δ 167.86, 165.14, 142.50, 138.26, 135.99, 131.91, 131.20, 129.60, 122.59, 120.86, 120.80, 117.05, 113.77, 53.81, 52.56, 36.47, 26.98, 23.02. ESI-MS m/z: 366.2 [M+H]$^+$; Purity: 98.1% by HPLC.

tert-Butyl 4-(1-carbamoyl-9H-pyrido[3,4-b]indole-3-carbonyl)piperazine-1-carboxylate (6r). $^1$H NMR (500 MHz, Chloroform-d) δ 10.37 (s, 1H), 8.58 (s, 1H), 8.16 (d, J=7.8 Hz, 1H), 7.76 (s, 1H), 7.69-7.53 (m, 2H), 7.36 (t, J=7.3 Hz, 1H), 5.79 (s, 1H), 3.86 (s, 2H), 3.72 (s, 2H), 3.60 (s, 2H), 3.52 (s, 2H), 1.49 (s, 9H). $^{13}$C NMR (125 MHz, CDCl$_3$) δ 168.49, 168.19, 154.80, 141.57, 141.43, 136.04, 132.43, 129.98, 129.20, 122.30, 121.23, 120.87, 119.74, 112.31, 80.55, 47.63, 42.75, 28.53. ESI-MS m/z: 424.3 [M+H]$^+$; Purity: 95.0% by HPLC.

3-(Piperazine-1-carbonyl)-9H-pyrido[3,4-b]indole-1-carboxamide (6s). $^1$H NMR (500 MHz, Deuterium Oxide) δ 7.41 (s, 1H), 7.12 (d, J=7.7 Hz, 1H), 7.06 (t, J=7.5 Hz, 1H), 6.84 (d, J=8.0 Hz, 1H), 6.71 (t, J=7.3 Hz, 1H), 3.79 (s, 4H), 3.29 (s, 2H), 3.17 (s, 2H). $^{13}$C NMR (125 MHz, D$_2$O) δ 168.18, 168.15, 140.32, 137.23, 133.82, 130.41, 129.12, 127.80, 120.66, 120.22, 118.86, 118.61, 111.50, 44.35, 43.16, 40.29, 39.76. ESI-MS m/z: 324.2 [M+H]$^+$; Purity: 96.0% by HPLC.

1-Carbamoyl-9H-pyrido[3,4-b]indole-3-carboxylic acid (6t). $^1$H NMR (500 MHz, Methanol-d$_4$) δ 8.96 (s, 1H), 8.19 (d, J=8.0 Hz, 1H), 7.66 (d, J=8.0 Hz, 1H), 7.54 (t, J=7.8 Hz, 1H), 7.27 (t, J=7.5 Hz, 1H). ESI-MS m/z: 254.2 [M−H]$^-$; Purity: 98.9% by HPLC.

3-((3aR,6aS)-Octahydropyrrolo[3,4-c]pyrrole-2-carbonyl)-9H-pyrido[3,4-b]indole-1-carboxamide (6u). $^1$H NMR (500 MHz, Deuterium Oxide) δ 7.38 (d, J=17.0 Hz, 1H), 7.29 (dt, J=11.8, 7.2 Hz, 2H), 7.08 (t, J=7.0 Hz, 1H), 6.95 (t, J=6.3 Hz, 1H), 3.67-3.63 (m, 2H), 3.58-3.53 (m, 2H), 3.49-3.41 (m, 2H), 3.25-3.21 (m, 1H), 3.12 (d, J=5.5 Hz, 1H), 3.10 (s, 2H). $^{13}$C NMR (125 MHz, D$_2$O) δ 168.00, 165.01, 140.32, 137.34, 133.46, 129.81, 129.06, 127.02, 120.76, 120.27, 119.18, 118.13, 111.61, 52.27, 50.84, 49.33, 48.97, 42.71, 39.03. ESI-MS m/z: 350.2 [M+H]$^+$; Purity: 97.8% by HPLC.

N$^3$-(2-Hydroxyethyl)-9H-pyrido[3,4-b]indole-1,3-dicarboxamide (6v). $^1$H NMR (500 MHz, DMSO-d$_6$) δ 11.94 (s, 1H), 9.34 (t, J=6.0 Hz, 1H), 9.06 (s, 1H), 8.99 (s, 1H), 8.41 (d, J=8.0 Hz, 1H), 7.90 (s, 1H), 7.84 (d, J=8.2 Hz, 1H), 7.60 (t, J=7.7 Hz, 1H), 7.30 (t, J=7.5 Hz, 1H), 4.80 (t, J=5.5 Hz, 1H), 3.58 (q, J=6.2 Hz, 2H), 3.45 (q, J=6.3 Hz, 2H). $^{13}$C NMR (125 MHz, DMSO) δ 167.47, 164.33, 141.99, 138.22, 135.47, 131.39, 130.73, 129.03, 122.13, 120.37, 120.31, 116.50, 113.25, 60.03, 41.78. ESI-MS m/z: 299.2 [M+H]$^+$; Purity: 97.3% by HPLC.

(R)-3-(3-Hydroxypyrrolidine-1-carbonyl)-9H-pyrido[3,4-b]indole-1-carboxamide (6w). $^1$H NMR (500 MHz, DMSO-d$_6$) δ 11.88 (s, 1H), 8.80 (d, J=7.1 Hz, 1H), 8.38 (d, J=7.7 Hz, 1H), 8.01 (s, 1H), 7.90 (d, J=10.2 Hz, 1H), 7.84 (d, J=8.2 Hz, 1H), 7.60 (t, J=7.6 Hz, 1H), 7.30 (t, J=7.5 Hz, 1H), 4.95 (m, 1H), 4.33 (d, J=16.0 Hz, 1H), 4.09 (q, J=5.2 Hz, 1H), 3.95 (t, J=9.2 Hz, 1H), 3.66 (m, 2H), 1.96 (m, 1H), 1.86 (m, 1H). $^{13}$C NMR (125 MHz, DMSO) δ 167.55, 165.88, 141.98, 141.59, 134.70, 131.19, 130.19, 130.10, 129.07, 122.08, 120.24, 118.64, 113.20, 69.90, 67.68, 57.19, 55.16, 48.60, 46.88, 44.93, 34.72, 31.83. ESI-MS m/z: 325.3 [M+H]$^+$; Purity: 95.2% by HPLC.

(S)-3-(3-Hydroxypyrrolidine-1-carbonyl)-9H-pyrido[3,4-b]indole-1-carboxamide (6x). $^1$H NMR (500 MHz, DMSO-d$_6$) δ $^1$H NMR (500 MHz, DMSO-d$_6$) δ 11.87 (s, 1H), 8.80 (d, J=7.0 Hz, 1H), 8.38 (d, J=7.6 Hz, 1H), 8.01 (s, 1H), 7.89 (d, J=10.5 Hz, 1H), 7.84 (d, J=8.2 Hz, 1H), 7.60 (t, J=7.6 Hz, 1H), 7.30 (t, J=7.4 Hz, 1H), 4.95 (d, J=48.4 Hz, 1H), 4.35-4.31 (m, 1H), 3.95 (dd, J=8.9, 3.5 Hz, 1H), 3.69-3.62 (m, 2H), 2.01-1.92 (m, 1H), 1.86 (t, J=6.8 Hz, 1H). $^{13}$C NMR (125 MHz, DMSO) δ 168.00, 166.35, 142.44, 142.05, 135.16, 131.65, 130.65, 130.56, 129.54, 122.55, 120.70, 119.10, 113.66, 70.36, 68.14, 57.65, 55.62, 47.34, 45.39, 35.18, 32.30. ESI-MS m/z: 325.3 [M+H]$^+$; Purity: 95.0% by HPLC.

Publications cited herein are hereby specifically incorporated by reference in their entireties and at least for the material for which they are cited.

It should be understood that while the present disclosure has been provided in detail with respect to certain illustrative and specific aspects thereof, it should not be considered limited to such, as numerous modifications are possible without departing from the broad spirit and scope of the present disclosure as defined in the appended claims. It is, therefore, intended that the appended claims cover all such equivalent variations as fall within the true spirit and scope of the invention.

What is claimed is:

1. A compound, having a structure defined by Formula I or a pharmaceutically acceptable salt thereof:

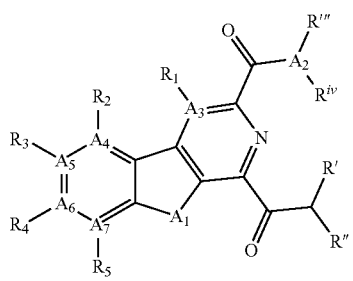

Fomula I wherein $A_1$ is selected from O, $CH_2$, S, or NH;
$A_2$ is N;
$A_3$, $A_4$, $A_5$, $A_6$, or $A_7$ are independently selected from C, S, N;
R' and R'' are independently selected from hydrogen or unsubstituted $C_1$-$C_6$ alkyl or both R' and R'' combine to form a substituted or unsubstituted $C_2$-$C_7$ heterocycloalkyl or a substituted or unsubstituted $C_2$-$C_7$ heterocycloalkenyl together with the atom to which they are attached;
R''' and R$^{iv}$ are independently selected from hydrogen; hydroxyl, substituted or unsubstituted $C_1$-$C_6$ alkyl, substituted or unsubstituted aminoalkyl, substituted or unsubstituted $C_1$-$C_6$ haloalkyl, substituted or unsubstituted cycloalkyl, substituted or unsubstituted cycloheteroalkyl, substituted or unsubstituted alkoxy, substituted or unsubstituted alkenyl, substituted or unsubstituted alkynyl, substituted or unsubstituted aryl, substituted or unsubstituted heteroaryl, or both R''' and R$^{iv}$ combine to form a substituted or unsubstituted $C_2$-$C_7$ heterocycloalkyl or a substituted or unsubstituted $C_2$-$C_7$ heterocycloalkenyl together with the atom to which they are attached;
$R_1$ is null or selected from hydrogen; hydroxyl, halide, substituted or unsubstituted nitrile, substituted or unsubstituted nitro, substituted or unsubstituted amine, substituted or unsubstituted alkyl halide, substituted or unsubstituted carboxyl, substituted or unsubstituted amide, substituted or unsubstituted ester, substituted or unsubstituted ether, substituted or unsubstituted ketone, substituted or unsubstituted $C_1$-$C_6$ alkyl, substituted or unsubstituted alkoxy, substituted or unsubstituted $C_2$-$C_6$ alkenyl, substituted or unsubstituted $C_2$-$C_6$ alkynyl, substituted or unsubstituted aryl, substituted or unsubstituted heteroaryl, substituted or unsubstituted silyl, substituted or unsubstituted sulfonyl, substituted or unsubstituted sulfone, substituted or unsubstituted sulfoxide, or substituted or unsubstituted thiol; and
$R_2$-$R_5$ are independently null or independently selected from hydrogen; hydroxyl, halide, substituted or unsubstituted nitrile, substituted or unsubstituted nitro, substituted or unsubstituted amine, substituted or unsubstituted alkyl halide, substituted or unsubstituted carboxyl, substituted or unsubstituted amide, substituted or unsubstituted ester, substituted or unsubstituted ether, substituted or unsubstituted ketone, substituted or unsubstituted $C_1$-$C_6$ alkyl, substituted or unsubstituted alkoxy, substituted or unsubstituted $C_2$-$C_6$ alkenyl, substituted or unsubstituted $C_2$-$C_6$ alkynyl, substituted or unsubstituted aryl, substituted or unsubstituted heteroaryl, substituted or unsubstituted silyl, substituted or unsubstituted sulfonyl, substituted or unsubstituted sulfone, substituted or unsubstituted sulfoxide, or substituted or unsubstituted thiol.

2. The compound of claim 1, having a structure defined by Formula I-B-1 or a pharmaceutically acceptable salt thereof:

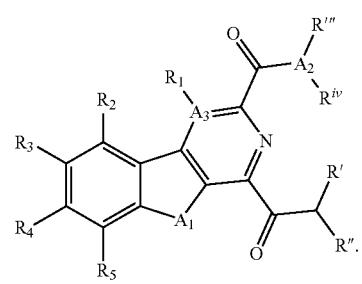

Fomula I-B-1

3. The compound of claim 1, or a pharmaceutically acceptable salt thereof, wherein $A_1$ is NH.

4. The compound of claim 1, or a pharmaceutically acceptable salt thereof, wherein $A_3$ is selected from C or N.

5. The compound of claim 1, or a pharmaceutically acceptable salt thereof, wherein R' and R'' are independently selected from hydrogen and unsubstituted $C_1$-$C_6$ alkyl or both R' and R'' combine to form a substituted or unsubstituted $C_2$-$C_7$ heterocycloalkyl together with the atom to which they are attached.

6. The compound of claim 1, or a pharmaceutically acceptable salt thereof, wherein R''' is hydrogen and R$^{iv}$ is independently selected from hydrogen; substituted or unsubstituted $C_1$-$C_6$ alkyl, substituted or unsubstituted aminoalkyl, substituted or unsubstituted $C_1$-$C_6$ haloalkyl, substituted or unsubstituted alkoxy, substituted or unsubstituted cycloalkyl, substituted or unsubstituted cycloheteroalkyl, substituted or unsubstituted aryl, substituted or unsubstituted heteroaryl, or
both R''' and R$^{iv}$ combine to form a substituted or unsubstituted $C_2$-$C_7$ heterocycloalkyl or a substituted or unsubstituted $C_2$-$C_7$ heterocycloalkenyl together with the atom to which they are attached.

7. The compound of claim 1, or a pharmaceutically acceptable salt thereof, wherein $R_1$ is selected from hydrogen; hydroxyl, halide, unsubstituted nitrile, unsubstituted nitro, unsubstituted amine, unsubstituted alkyl halide, unsubstituted carboxyl, unsubstituted amide, unsubstituted ester, unsubstituted ether, unsubstituted $C_1$-$C_6$ alkyl, unsubstituted alkoxy, unsubstituted $C_2$-$C_6$ alkenyl, substituted or unsubstituted aryl, substituted or unsubstituted heteroaryl, or unsubstituted thiol.

8. The compound of claim 1, or a pharmaceutically acceptable salt thereof, wherein $R_2$ is selected from hydrogen; hydroxyl, halide, unsubstituted nitrile, unsubstituted nitro, unsubstituted amine, unsubstituted alkyl halide, unsubstituted carboxyl, unsubstituted amide, unsubstituted ester, unsubstituted ether, unsubstituted $C_1$-$C_6$ alkyl, unsubstituted alkoxy, unsubstituted $C_2$-$C_6$ alkenyl, substituted or unsubstituted aryl, substituted or unsubstituted heteroaryl, or unsubstituted thiol.

9. The compound of claim 1, or a pharmaceutically acceptable salt thereof, wherein $R_3$ is selected from hydrogen; hydroxyl, halide, unsubstituted nitrile, unsubstituted nitro, unsubstituted amine, unsubstituted alkyl halide, unsubstituted carboxyl, unsubstituted amide, unsubstituted ester, unsubstituted ether, unsubstituted $C_1$-$C_6$ alkyl, unsubstituted alkoxy, unsubstituted $C_2$-$C_6$ alkenyl, substituted or unsubstituted aryl, substituted or unsubstituted heteroaryl, or unsubstituted thiol.

10. The compound of claim 1, or a pharmaceutically acceptable salt thereof, wherein $R_4$ is selected from hydrogen; hydroxyl, halide, unsubstituted nitrile, unsubstituted nitro, unsubstituted amine, unsubstituted alkyl halide, unsubstituted carboxyl, unsubstituted amide, unsubstituted ester, unsubstituted ether, unsubstituted $C_1$-$C_6$ alkyl, unsubstituted alkoxy, unsubstituted $C_2$-$C_6$ alkenyl, substituted or unsubstituted aryl, substituted or unsubstituted heteroaryl, or unsubstituted thiol.

11. The compound of claim 1, or a pharmaceutically acceptable salt thereof, wherein $R_5$ is selected from hydrogen; hydroxyl, halide, unsubstituted nitrile, unsubstituted nitro, unsubstituted amine, unsubstituted alkyl halide, unsubstituted carboxyl, unsubstituted amide, unsubstituted ester, unsubstituted ether, unsubstituted $C_1$-$C_6$ alkyl, unsubstituted alkoxy, unsubstituted $C_2$-$C_6$ alkenyl, substituted or unsubstituted aryl, substituted or unsubstituted heteroaryl, or unsubstituted thiol.

12. The compound of claim 1, or a pharmaceutically acceptable salt thereof, wherein $R_2$-$R_5$ are independently selected from hydrogen; halide, or unsubstituted $C_1$-$C_6$ alkyl.

13. The compound of claim 1, having a structure selected from Formula 6a-6x

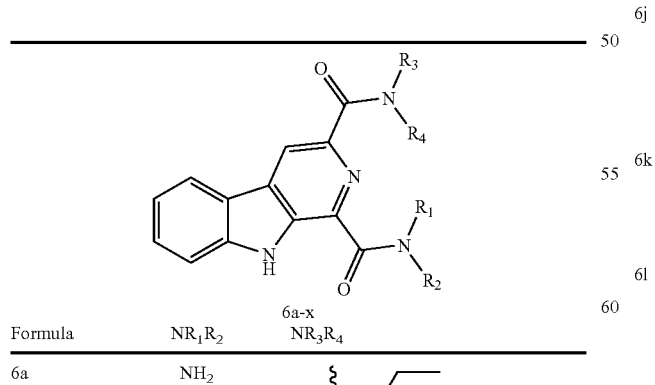

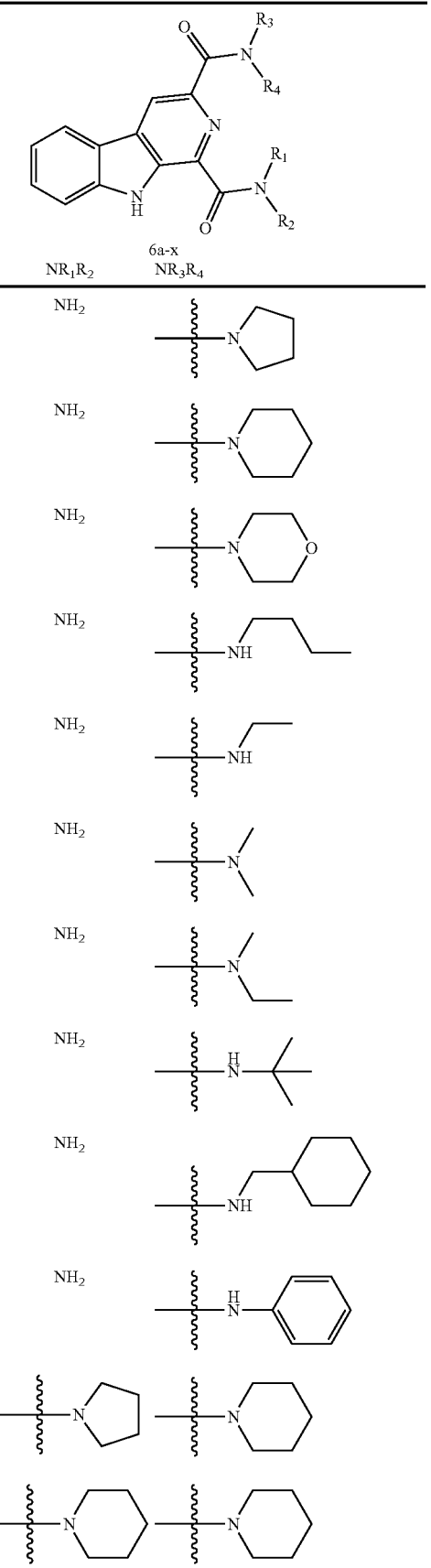

-continued
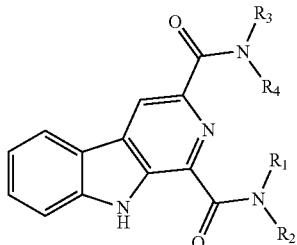
| Formula | NR₁R₂ | NR₃R₄ |
|---|---|---|
| 6n | NH₂ | 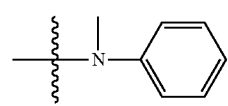 |
| 6o | NH₂ | 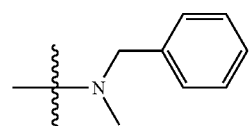 |
| 6p | NH₂ | 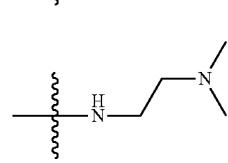 |
| 6q | NH₂ | 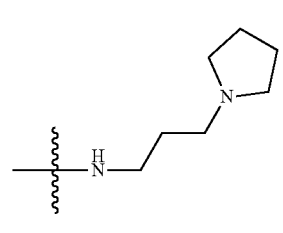 [SMILES: *NCCCN1CCCC1] |
| 6r | NH₂ | 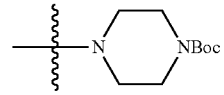 |
| 6s | NH₂ | 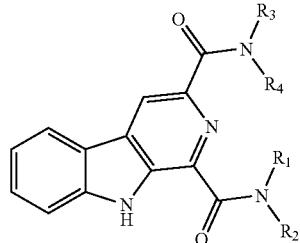 |
| 6t | NH₂ | 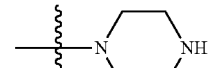 |
| 6u | NH₂ | 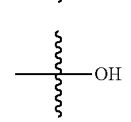 |
| 6v | NH₂ | 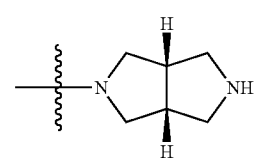 [SMILES: *N1C[C@H]2CNC[C@H]2C1] |
| 6w | NH₂ | 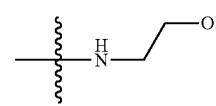 |
| 6x | NH₂ | 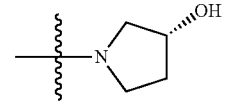 [SMILES: *N1CC[C@@H](O)C1] |
or a pharmaceutically acceptable salt thereof.
* * * * *